(12) United States Patent
Liu et al.

(10) Patent No.: US 8,815,561 B2
(45) Date of Patent: Aug. 26, 2014

(54) METAL COMPOUNDS TO ELIMINATE NONPRODUCTIVE ENZYME ADSORPTION AND ENHANCE ENZYMATIC SACCHARIFICATION OF LIGNOCELLULOSE

(75) Inventors: Hao Liu, Madison, WI (US); Junyoug Zhu, Madison, WI (US)

(73) Assignees: Wisconsin Alumni Research Foundation, Madison, WI (US); The United States of America as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 13/215,729

(22) Filed: Aug. 23, 2011

(65) Prior Publication Data
US 2012/0070864 A1 Mar. 22, 2012

Related U.S. Application Data

(60) Provisional application No. 61/376,139, filed on Aug. 23, 2010.

(51) Int. Cl.
*C12N 9/42* (2006.01)
*C12P 7/10* (2006.01)

(52) U.S. Cl.
USPC .............................. 435/209; 435/165; 435/99

(58) Field of Classification Search
None
See application file for complete search history.

(56) References Cited

U.S. PATENT DOCUMENTS

| | | | |
|---|---|---|---|
| 2,269,985 A | 1/1942 | Olsen | 162/79 |
| 2,924,547 A | 2/1960 | Knapp et al. | 162/83 |
| 3,808,090 A | 4/1974 | Logan et al. | 162/23 |
| 3,998,688 A | 12/1976 | Fischer et al. | 162/50 |
| 3,998,845 A | 12/1976 | Goldstein et al. | 549/87 |
| 4,017,642 A | 4/1977 | Orth et al. | 426/69 |
| 4,211,605 A | 7/1980 | Saxton et al. | 162/64 |
| 4,461,468 A | 7/1984 | Peter et al. | 271/308 |
| 4,767,499 A | 8/1988 | Simonson et al. | 162/25 |
| 5,004,523 A | 4/1991 | Springer et al. | 162/76 |
| 5,205,496 A | 4/1993 | O'Donnell et al. | 241/34 |
| 5,597,714 A | 1/1997 | Farone et al. | 435/100 |
| 5,676,795 A | 10/1997 | Wizani et al. | 162/30.11 |
| 5,916,780 A | 6/1999 | Foody et al. | 435/99 |
| 6,017,870 A | 1/2000 | Bower et al. | 510/392 |
| 6,027,610 A | 2/2000 | Back et al. | 162/111 |
| 6,555,350 B2 | 4/2003 | Ahring et al. | 435/162 |
| 7,182,836 B2 | 2/2007 | Patt et al. | 162/90 |
| 2002/0026991 A1 | 3/2002 | Stromberg et al. | 162/19 |
| 2003/0098272 A1 | 5/2003 | Marsh et al. | 210/321.74 |
| 2005/0207971 A1 | 9/2005 | Cortright et al. | 423/657 |
| 2009/0229771 A1 | 9/2009 | Warnes et al. | 162/28 |
| 2009/0298149 A1 | 12/2009 | Wang et al. | 435/165 |

FOREIGN PATENT DOCUMENTS

| | | |
|---|---|---|
| EP | 0 105 937 | 4/1984 |
| WO | WO 2008151043 A1 * | 12/2008 |

OTHER PUBLICATIONS

Urbanowicz B. et al. Structural Organization and a Standardized Nomenclature for Plant Endo-1,4-beta-glucanases (Cellulases) of Glycosyl Hydrolase Family 9. 2007. Plant Physiology. 144. 1693-1696.*
Allen et al, "A comparison of aqueous and dilute-acid single-temperature pretreatment of yellow of poplar sawdust," *Ind. Eng. Chem. Res.*, 40:2352-2361, 2001.
Ballesteros et al., "Effect of chip size on steam explosion pretreatment of softwood," *Applied Biochem. Biotechnol.*, 84-86:97-110, 2000.
Bhardwaj et al., "Pulp charge determination by different methods: effect of beating/refining," *Colloids and Surface A: Physiochem. Eng. Aspects*, 236:39-44, 2004.
Borjesson et al., "Enhanced enzymatic conversion of softwood lignocellulose by poly(ethylene glycol) addition," *Enzyme and Microbial Techol.*, 40(5): 754-762, 2007.
Cadoche and López, "Assessment of size reduction as a preliminary step in the production of ethanol from lignocellulosic wastes," *Biological Wastes*, 30:153-157, 1989.
Chen et al., "New process of maize stalk amination treatment by steam explosion," *Biomass and Bioenergy*, 28:411-417, 2005.
Chum et al., "Pretreatment-catalyst effects of the combined severity parameter," *Appl. Biochem. Biotechnol.*, 24-25:1-14, 1990.
Chundawat et al., "Effect of particle size based separation of milled corn stover on AFEX pretreatment and enzymatic digestibility," *Biotechnol. Bioengineer.*, 85:219-231, 2007.
Crist et al., "A new process for toxic metal uptake by a kraft lignin," *J. Chem. Technol. Biotechnol.*, 78:199-202, 2003.
Cullis et al., "Effect of initial moisture content and chip size on the bioconversion efficiency of softwood lignocellulosics," *Biotechnol. Bioengineer.*, 85:413-421, 2004.
Dasari and Berson, "The effect of particle size on hydrolysis reaction rates and rheological properties in cellulosic slurries," *Applied Biochem. Biotech.*, 137:289-299, 2007.
Davis, "A rapid modified method for compositional carbohydrate analysis of lignocellulosics by high ph anion-exchange chromatography with pulsed amperometric detection (HPAEC/PAD)," *J. Wood Chem. Tech.*, 18(2): 235-252, 1998.

(Continued)

*Primary Examiner* — David J Steadman
*Assistant Examiner* — Paul Holland
(74) *Attorney, Agent, or Firm* — Parker Highlander PLLC

(57) ABSTRACT

Methods and composition for biofuel processing are provided. For example, in certain aspects methods for using metal compounds to enhance cellulose enzymatic hydrolysis are described. Furthermore, the invention provides integrated processes with fewer lignin removal steps to improve efficiency.

16 Claims, 27 Drawing Sheets

(56) References Cited

OTHER PUBLICATIONS

De Bari et al., "$SO_2$-catalyzed steam fractionation of aspen chips for bioethanol production: optimization of the catalyst impregnation," *Ind. Eng. Chem. Res.*, 46:7711-7720, 2007.
Eggeman and Elander, "Process and economic analysis of pretreatment technologies," *Bioresour. Technol.*, 96:2019-2025, 2005.
Eriksson et al., "Mechanism of surfactant effect in enzymatic hydrolysis of lignocellulose," *Enzyme Microb. Technol.*, 31(3) 353-364, 2002.
Excoffier et al., "Saccharification of steam-exploded poplar wood," *Biotechnol. Bioeng.*, 38:1308-1317, 1991.
Galbe and Zacchi, "A review of the production of ethanol from softwood," *Appl. Microbiol. Biotech.*, 59:618-628, 2002.
Grierson et al., "The role of calcium ions and lignosulphonate plasticiser in the hydration of cement," *Cement Concrete Res.*, 35:631-636, 2005.
Guo et al., "Adsorption of metal ions on lignin," *J. Hazardous Mat.*, 151(1): 134-142, 2008.
Guy et al., In: *Comparison of fiber length analyzers*, Proc. 2005 TAPPI Papermarkers Conf., Milwaukee, WI, 2005.
Heitz et al., "Fractionation of *Populas tremuloides* at the pilot scale: optimization of steam explosion pretreatment conditions using the STAKE II technology," *Bioresour. Technol.*, 35:23-32, 1991.
Helle et al., "Effect of surfactants on cellulose hydrolysis," *Biotechnol. Biogengineer.*, 42:611-617,1993.
Himmel et al., "Biomass recalcitrance: engineering plants and enzymes for biofuels production," *Science*, 315:804-807, 2007.
Holtzapple et al., "Energy requirements for the size reduction of poplar and aspen wood," *Biotech. Bioeng.*, 33:207-210, 1989.
Hoque et al., In: *Review and anlysis of performance and productivity of size equipment for fibrous materials*, ASABE Annual International Meeting, Minneappolis, MN, 2007.
Jeoh et al., "Cellulase digestibility of pretreated biomass is limited by cellulose accessibility," *Biotechnol. Bioeng.*, 98:112-122, 2007.
Katz et al., "The determination of strong and weak acidic groups in sulfite pulps," *Svensk Paperstidn*, 87:48-53, 1984.
Kenealy et al., "Vapor phase diethyl oxalate pretreatment of wood chips: Part 1, energy saving and improved pulps," *Holzforschung*, 61:223-229, 2007.
Larsson et al., "The generation of fermentation inhibitors during dilute acid hydrolysis of softwood," *Enzyme Microbial. Tech.*, 24:151-159, 1999.
Laureano-Perez et al., "Understanding factors that limit enzymatic hydrolysis of biomass: characterization of pretreated corn stover," *Appl. Biochem. Biotech.*, 121-124:1081-1099, 2005.
Lindgren, "Treatment of spruce lignin with sulphite solutions at pH 4-9," *Acta. Chemica Scandinavia*, 5:603-615, 1951.
Liu et al., "Effects of lignin-metal complexation on enzymatic hydrolysis of cellulose," *J. Agric. Food Chem.*, 58(12):7233-7238, 2010.
Lynd et al., "Biocommodity Engineering," *Biotechnol. Prog.*, 15(5):777-793, 1999.
Lynd, "Overview and evaluation of fuel ethanol from cellulosic biomass: technology, economics, the environment, and policy," *Annu. Rev. Energy and the Environment*, 21:403-465, 1996.
Mabee et al., "Updates on softwood-to-ethanol process development," *Appl. Biochem. Biotech.*, 129-132:55-70, 2006.
Mani et al., "Grinding performance and physical properties of wheat and barley straws, corn stover and switchgrass," *Biomass. and Bioenergy*, 27:339-352, 2004.
Mansfield et al., "Substrate and enzyme characterization that limit cellulose hydrolysis," *Biotech. Progress*, 15:804-816, 1999.
Mizutani et al., "Effect of a nonionic surfactant on *Trichoderma* cellulase treatments of regenerated cellulose and cotton yarns," *Cellulose*, 9(1): 83-89, 2002.
Mooney et al., "The effect of fiber characteristics on hydrolysis and cellulase accessibility to softwood substrates," *Enzyme and Microbial. Technol.*, 25:644-650, 1999.

Mosier et al., "Features of promising technologies for pretreatment of lignocellulosic biomass," *Bioresour. Tech.*, 96:673-686, 2005.
Nagle et al., "Efficacy of a hot washing process for pretreated yellow poplar to enhance bioethanol production," *Biotechnol. Prog.*, 18(4): 734-738, 2002.
Nguyen et al., "Two-stage dilute-acid pretreatment of softwoods," *Appl. Biochem. Biotech.*, 84-86:561-576, 2000.
Öhgren et al., "Optimization of steam pretreatment of $SO_2$-impregnated corn stover for fuel ethanol production," *Appl. Biochem. Biotech.*, 121-124: 1055-1068, 2005.
Ooshima et al., "Adsorption of cellulase from *Trichoderma reesei* on cellulose and lignacious residue in wood pretreated by dilute sulfuric acid with explosive decomposition," *Biotechnol. Bioeng.*, 36(5): 446-452, 1990.
Ooshima et al., "Enhancement of enzymatic hydrolysis of cellulose by surfactant," *Biotech. Bioeng.*, XXVIII: 1727-1734, 1986.
Pan et al., "Bioconversion of hybrid poplar to ethanol and co-products using an organosolv fractionation process: optimization of process yields," *Biotech. Bioengin.*, 94:851-861, 2006.
Pan et al., "Biorefining of softwoods using ethanol organosolv pulping: preliminary evaluation of process streams for manufacture of fuel-grade ethanol and co-products," *Biotech. Bioengin.*, 90:473-481, 2005.
Pan et al., "Enhanced enzymatic hydrolysis of steam-exploded Douglas fir wood by alkali-oxygen post-treatment," *Appl. Biochem. Biotechnol.*, 113-116: 1103-1114, 2004.
Pan et al., "Strategies to enhance the enzymatic hydrolysis of pretreated softwood with high residual lignin content," *Appl. Biochem. Biotechnol.*, 121-124:1069-1079, 2005.
Pan et al., "The bioconversion of mountain pine beetle-killed lodgepole pine to fuel ethanol using the organosolv process," *Biotechnol. Bioeng.*, 101(1):39-48, 2008.
Reinke, "A new multiple-unit constant-pressure micro-respirometer," *J. Appl. Physiol.*, 16:944-946, 1961.
Rivers and Emert, "Lignocellulose pretreatment: a comparison of wet and dry ball attrition," *Biotechnology Letters*, 9:365-8, 1987.
Salmon, "Determination of malolactic enzyme activity using an immobilized L-lactate oxidase probe," *Biotechnol. Tech.*, 5(5): 383-388, 1991.
Sangseethong et al., "Rationale for particular size effect on rates enzymatic saccharification of microcrystalline cellulose," *J. Food. Biochem.*, 22:321-330, 1998.
Schell and Harwood, "Milling of lignocellulosic biomass: results of pilot scale testing," *Appl. Biochem. Biotech.*, 45/46:159-168, 1994.
Sewalt et al, "Lignin impact on fiber degradation. 3. Reversal of inhibition of enzymatic hydrolysis by chemical modification of lignin and by additives.," *J. Agric. Food Chem.*, 45(5): 1823-1828, 1997.
Simola et al., "Scanning probe microscopy of pine and birch kraft pulp fibres," *Polymer*, 41:2121-2126, 2000.
Sinitysyn et al., "Inhibition of cellulases by impurities in Steam-Exploded wood," *Appl. Biochem. Biotech.*, 7(6): 455-458, 1982.
Stenberg et al., "Effect of substrate and cellulase concentration on simultaneous saccharification and fermentation of steam-pretreated softwood for ethanol production," *Biotechnol. Bioeng.*, 68:204-10, 2000.
Sun and Cheng, "Hydrolysis of lignocellulosic materials for ethanol production: a review," *Bioresource Technol*, 83:1-11, 2002.
Tengborg et al., "Reduced inhibition of enzymatic hydrolysis of steam-pretreated softwood," *Enzyme Microb. Technol.*, 28(9-10): 835-844, 2001.
Tillman et al., "Effect of transient variation of temperature on acid hydrolysis of aspen hemicellulose," *Applied Biochem. Biotechnol.*, 20-21:107-117, 1989.
Tillman et al., "Effect of transient acid diffusion on pretreatment/ hydrolysis of hardwood hemicellulose," *Applied Biochem. Biotechnol.*, 24-25:103-113, 1990.
Torre et al., "Study of the interactions of calcium ions with lignin, cellulose, and pectin," *J. Agric. Food Chem.*, 40(1): 1762-1766, 1992.
Tu et al., "Effect of surfactants on separate hydrolysis fermentation and simultaneous saccharification fermentation of pretreated lodgepole pine," *Biotechnol. Prog.*, 25(4): 1122-1129, 2009.

(56) References Cited

OTHER PUBLICATIONS

Wang et al., "Sulfite pretreatment to overcome recalcitrance of lignocellulose (SPORL) for robust enzymatic saccharification of hardwoods," *Biotech. Prog.*, 25(4): 1086-1093, 2009.

Wingren et al., "Techno-economic evaluation of producing ethanol from softwood: comparison of SSF and SHF and identification of bottlenecks," *Biotechnol. Prog.*, 19:1109-1117, 2003.

Xu et al., "Lignin precipitation on the pulp fibers in the ethanol-based organosolv pulping," *Colloids and Surfaces A: Physicochemical and Engineering Aspects*, 301 (1-3): 255-263, 2007.

Yang and Wyman, "BSA treatment to enhance enzymatic hydrolysis of cellulose in lignin containing substrates," *Biotech. Bioeng.*, 94(4): 611-617, 2006.

Yang and Wyman, "Effect of xylan and lignin removal by batch and flowthrough pretreatment on the enzymatic digestibility of corn stover cellulose," *Biotech. Bioengin.*, 86:88-95, 2004.

Yean et al., "A fundamental investigation of the influence of liquor composition and temperature on the rate of solution of wood material," *Pulp and Paper Magazine of Canada*, 58(7): 197-210, 1957.

Zhao et al., "Enhanced enzymatic hydrolysis of spruce by alkaline pretreatment at low temperature," *Biotechnol. Bioengin.*, 99:1320-1328, 2008.

Zheng et al., "Non-ionic Surfactants and Non-Catalytic Protein Treatment on Enzymatic Hydrolysis of Pretreated Creeping Wild Ryegrass," *Appl. Biochem. Biotechnol.*, 146:231-248, 2008.

Zhu et al., "Effects of plantation density on wood density anatomical properties of red pine (*Pinus resinosa* ait)," *Wood and Fiber Sci.*, 39:502-512, 2007.

Zhu et al., "Ethanol production from SPORL-pretreated lodgepole pine: preliminary evaluation of mass balance and process energy efficiency," *Appl. Microbiol. Biotechnol.*, 86(5): 1355-1365, 2010.

Zhu et al., "On energy consumption for size-reduction and yields from subsequent enzymatic saccharification of pretreated lodgepole pine," *Bioresour. Technol.*, 101(8): 2782-2792, 2010.

Zhu et al., "Optimization of dilute-acid pretreatment of corn stover using a high-solids percolation reactor," *Biochem. Biotech.*, 121-124:1045-1054, 2005.

Zhu et al., "Specific surface to evaluate the efficiencies of milling and pretreatment of wood enzymatic saccharification," *Chem. Eng. Sci.*, 64:474-485, 2009.

Zhu et al., "Sulfite pretreatment (SPORL) for robust enzymatic saccharification of spruce and red pine," *Bioresource Technology*, 100:2411-2418, 2009.

Zhu and Pan, "Woody biomass pretreatment for cellulosic ethanol production: Technology and energy consumption evaluation," *Bioresour. Technol.*, 101(13): 4992-5002, 2010.

* cited by examiner

METAL COMPOUNDS TO ELIMINATE NONPRODUCTIVE ENZYME ADSORPTION AND ENHANCE ENZYMATIC SACCHARIFICATION OF LIGNOCELLULOSE

This application claims priority to U.S. Application No. 61/376,139 filed on Aug. 23, 2010, the entire content of which is hereby incorporated by reference in its entirety without disclaimer.

This invention was made with government support under 09-JV-11111122-027 awarded by the USDA/FS. The government has certain rights in the invention. Inventor JunYong Zhu is a federal employee.

BACKGROUND OF THE INVENTION

1. Field of the Invention

The present invention relates generally to the field of biomass biorefining. More particularly, it concerns using metal compounds to enhance enzymatic hydrolysis of biomass material.

2. Description of Related Art

Lignocellulose biomass is considered a very desirable feedstock for biofuel production. Researchers have speculated that conversion of lignocellulose material could yield 25-50 billion gallons of ethanol per year if the fermentation process for lignocellulose can be optimized. As lignocellulose is a complex structural material made up of lignin, cellulose, and hemicellulose; a pretreatment step might be required to make the material amenable to cellulytic hydrolysis to convert the cellulose into fermentable sugars. Enzyme accessibility of the starting material is one of the key limiting steps for hydrolysis of lignocellulose in biorefining of biomass.

It has been recognized that lignin is one of the key, nonproductive enzyme adsorption medium present in this material. Generally, lignin needs to be removed or at least reduced from the pretreated lignocellulosic substrate through an initial washing and separation step wherein cellulose is isolated for enzymatic saccharification and fermenting into biofuel. The initial washing steps typically involve use of copious amounts of water and include high temperatures leading to significant amounts of water and energy consumption, which not only increases costs, but also presents a serious environmental concern. Exogenous protein (bovine serum albumin-BSA) has been used to mask lignin to reduce adsorption of cellulase onto lignin enhancing enzymatic cellulose saccharification. Surfactants have also been used as lignin-block agents to improve enzymatic hydrolysis. Both of these techniques have hurdles that prohibit commercial applications. Proteins are too expensive to use in large scale production. Surfactants can cause foaming which may negatively impact saccharification and fermentation, and can also be expensive at its effective dosage.

Therefore, there exists a need for new methods to inhibit enzyme absorption by lignin during the biofuel production.

SUMMARY OF THE INVENTION

Aspects of the present invention overcome a major deficiency in the art by providing novel methods for enhancing lignocellulose hydrolysis, as well as cellulose hydrolyzing compositions. Accordingly, in a first embodiment there is provided a cellulose hydrolyzing composition. The composition may comprise a material comprising cellulose and lignin, a divalent metal, in the form of base or salt, and a cellulase enzyme. The material may comprise a solid or a mixture of a solid and a liquid, such as slurry. In particular aspects, the lignin may comprise lignosulfonate, which may be present at least or about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.30, 0.40, 0.50, 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 20, 30, 40, 50, 60, 70, 80, 90, 100 g/L of total lignin or any range or value derivable therein. The lignosulfonate may be present in at least or about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 30 weight percent (or any percent derivable therein) of the composition.

For example, the divalent metal may comprise calcium or magnesium in an aqueous solution. The aqueous solution may be at a pH of 1, 2, 3, 4, 5, 6, 7, 8, 9, 10 or any range derivable therein. In particular, the pH may be about 2 to 8, or more particularly, about 4 to 7. For example, the metal may be present at an amount of about 0.01 mol to 10 mol per kg solid material, or more particularly, about 0.1 mol to 4 mol per kg solid material, or any range or value derivable therein. The divalent metal in the composition may increase enzymatic cellulose hydrolysis as compared to enzymatic cellulose hydrolysis in the absence of the divalent metal.

In further aspects, the composition may comprise hydrolyzed hemicellulose. For biofuel production, the composition may also comprise organisms such as microorganisms that covert hydrolyzed cellulose into ethanol, microorganisms that covert hydrolyzed hemicellulose into ethanol or a combination thereof, particularly fermentative organisms.

In addition, there may be provided a method for cellulose hydrolysis. The method may comprise providing a cellulose hydrolyzing composition described above and treating the composition under conditions which hydrolyze cellulose, thereby hydrolyzing the cellulose in the material of the composition. To provide the composition, the method may comprise pretreating a lignocellulosic material with a sulfite or bisulfate or sulfur dioxide. The method may further comprise reducing the size of the pretreated material, such as disk milling. By reducing the inhibitory effect of unbound lignin which may be provided by the added metal, the method may obviate the need to wash the material to remove unbound lignin, thus saving energy and costs. The method may comprise separating the pretreated material into a solid portion and a liquid portion (such as pretreatment hydrolysate). The method may further comprise adding the divalent metal to the solid or liquid portion. The cellulase may be added to the solid portion for enzymatic hydrolysis prior to, during or after the addition of metals. The composition may be provided by mixing the liquid portion having the divalent metal, the solid portion and a cellulase, and converting the resulting mixture into biofuels or biochemicals such as by fermentation. As an additional advantage, the method may comprise not removing fermentation inhibitors from the liquid portion (such as detoxification). The method may further comprise producing biofuels from hydrolyzed cellulose, such as fermentation or using chemicals or enzymes that mimic fermentative organisms.

The method may comprise the steps of: a) mixing a composition comprising a solid material with an aqueous solution comprising a divalent metal compound that increases enzymatic cellulose hydrolysis as compared with that in the absence of such a metal compound, wherein the solid material contains cellulose and lignin; and b) treating the mixture with at least a cellulase enzyme under conditions which hydrolyze cellulose, thereby providing hydrolyzed cellulose. The methods may involve the use of lignin-metal complexation or similar associations to reduce or eliminate nonproductive enzyme absorption by lignin and/or other inhibitory substances in lignocellulose enzymatic hydrolysis. For example, the metal may be in the form of a metal salt or base. In particular aspects, the metal compound may comprise a calcium or magnesium compound, more particularly, in the form of a calcium or magnesium salt or oxide. The metal may be in the form of $CaCl_2$, $CaCO_3$, $CaSO_4$, $MgSO_4$, $Ca(OH)_2$, CaO, or a combination thereof.

Non-limiting examples of cellulase enzyme include endoglucanase, exogluocanase, β-glucosadase or a combination thereof. The enzyme may be present at a concentration of about 0.001, 0.005, 0.01, 0.05, 0.1, 0.5, 1, 2, 3, 4, 5, 6, 7, 8, 9, 10 mol per kilogram solid material or any intermediate ranges or numbers, or less than the concentration effective for cellulose hydrolysis wherein such divalent metal compound is not added.

In certain aspects, the solid material (substrate) contains a lignin concentration (the lignin may include lignin bound to the solid material, not necessarily chemically bound, and/or lignin unbound and removable by a pretreatment step) of about 0.1, 0.5, 1, 5, 10, 15, 20, 25, 30, 35, 40, 45, 50, 55, 60, 65, 70, 75, 80, 90, 95, 99 percent or any intermediate ranges or numbers. For example, the solid material may have a lignin content of about 0.1 to 95%, more specifically, 5 to 50%. In further aspects, the divalent metal compound may be mixed with the solid material at about 0.01, 0.05, 0.1, 0.5, 1, 2, 3, 4, 5, 6, 7, 8, 9, 10 mol per kilogram solid material or any intermediate ranges or numbers. The mixing of solid material and the divalent metal compound may occur at a temperature of about 5, 10, 15, 20, 25, 30, 37, 40, 45, 50, 55, 60, 65, 70, 75° C. or any range derivable therein.

In further aspects, the method may further comprise pretreating a lignocellulosic material to disrupt its fiber structure for providing the solid material. The lignocellulosic material may be any woody and non-woody (e.g., herbaceous) biomass feedstock, including grasses, agriculture residues, municipal solid waste, waste paper, softwood, and/or hardwood.

Non-limiting examples of pretreatment may comprise sulfite pretreatment to overcome recalcitrance of lignocellulose (SPORL), size reduction, acid hydrolysis, hot water pretreatment, steam explosion (including acid or $SO_2$ catalyzed), aqueous ammonia, ammonia fiber expansion, alkaline, Organosolv pretreatment, alkaline wet oxidation ozone pretreatment, or a combination thereof. Specifically, the method or the pretreatment comprises SPORL and/or size reduction such as disk milling.

In common practice, a thorough washing is applied to remove unbound (detached from lignocellulosic solid substrate) lignin and other inhibitory substances and thereby reduce nonproductive enzyme absorption during lignocellulose solid substrate enzymatic hydrolysis. The benefit of the formation of lignin-metal complex with unbound or bound (not yet separated from lignocellulosic solid substrate, not necessary chemically bound) lignin as disclosed in certain aspects of this invention is to avoid the energy and water cost in heavy washing. For example, the method or the pretreatment step may have no washing involved.

The compositions and methods described herein can be used to produce sugars (mainly glucose) through enzyme processing for the production of any number of biofuels. Biofuels include, without limitation, alcohols such as ethanol, methanol, propanol, and butanol, solvents such as acetone, and blends thereof. Although ethanol may be the predominant biofuel referred to in the disclosure herein, such use of 'ethanol' is not meant to limit any of the present disclosure. The methods and compositions can be used to prepare biomass for conversion to sugars that would subsequently be used to produce other biofuels including without limitation other alcohols (such as butanol) jet fuel, and biodiesel.

The method may further comprise producing ethanol and/or biofuel from hydrolyzed cellulose, such as fermentation. In one aspect, the method may comprise cellulose hydrolysis and production of biofuel (e.g., ethanol) in separate reactors (e.g., separate enzyme hydrolysis and fermentation). In other aspects, it might be advantageous to have cellulose hydrolysis and production of ethanol and/or biofuel in the same reactor (e.g., simultaneous saccharification and fermentation (SSF) or simultaneous saccharification and combined fermentation (SSCombF) of cellulose and hemicellulose fractions).

In some further aspects, the pretreatment provides a liquid portion containing hydrolyzed hemicellulose. The method may also comprise separating the solid material from the liquid portion. For hemicellulose bioconversion, the method may also comprise producing ethanol, biochemicals, bioproducts and/or biofuel from the separated liquid portion. In a particular aspect, the method may further comprise mixing the separated liquid portion with hydrolyzed cellulose and producing ethanol, biochemicals, bio-products and/or biofuel from the resulting mixture (e.g., combined fermentation of pretreatment and enzyme hydrolysates). For example, detoxification of pretreatment hydrolysates or the hemicellulose-containing liquid portion may be eliminated.

For further process simplification and improvement, the composition in the step a) may further comprise hydrolyzed hemicellulose. The method may further comprise cellulose hydrolysis and production of ethanol, biochemicals, bioproducts and/or biofuel from hydrolyzed cellulose and hydrolyzed hemicellulose in the same reactor or in a single step because of the effect of metal compound in enhancing enzymatic hydrolysis.

Certain embodiments of the invention are also directed to a product comprising ethanol, biofuel, biochemicals, or bio-products produced by the methods in accordance with any of the above embodiments.

Embodiments discussed in the context of methods and/or compositions of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 13A. Correlations between the amount of washing water application and lignin concentration in the washing filtrate stream. FIG. 13B. The effect of washing water temperature on the maximal amount of removable unbound lignin (MARUL).

DESCRIPTION OF ILLUSTRATIVE EMBODIMENTS

I. Introduction

Figure 1:
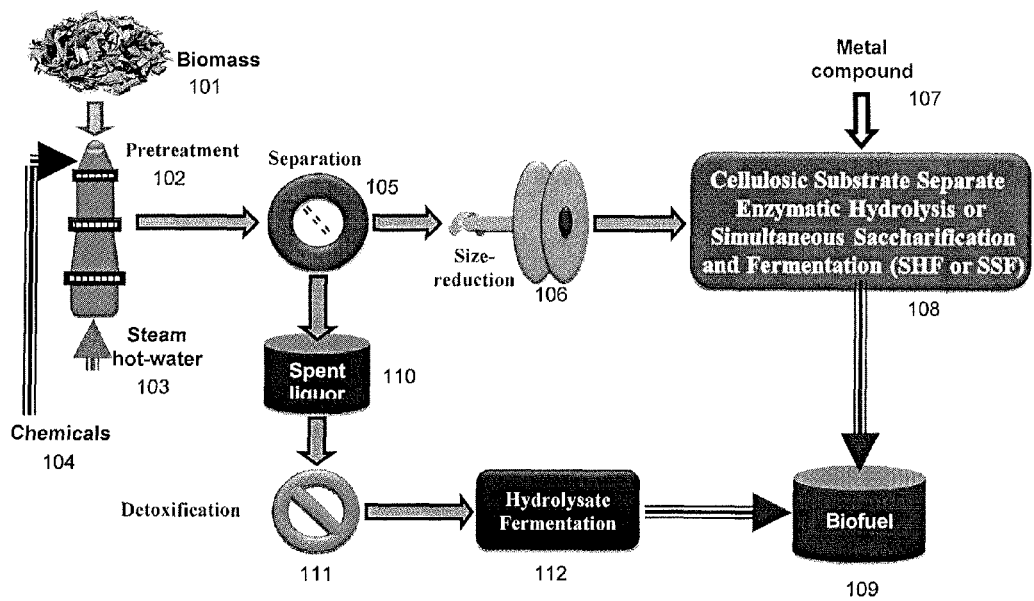
FIG. 1. An exemplary embodiment of biofuel production process flow.

This invention relates to reduction or elimination of inhibitive processes in enzymatic hydrolysis of lignocelluloses by preventing non-productive adsorption of enzymes onto compounds in enzyme and lignocellulose systems. More specifically, it relates to using divalent compounds, such as metal salts of calcium (Ca) and magnesium (Mg), metal oxide of calcium (Ca) and magnesium (Mg), to bind with lignin in aqueous enzyme and lignocellulose systems to form lignin-metal complex to deactivate nonproductive adsorption sites on lignin for enzymes. As a result, more enzymes are available to cellulose for more efficient cellulose saccharification. When lignin is sulfonated, such as lignin from sulfite pretreatments, $SO_2$ catalyzed steam explosion and SPORL, the formation of divalent metal-lignin complex, a lignosulfonate, may act as a surfactant to enhance enzymatic hydrolysis without the negative effect of lignin caused reduced enzyme activities through non-productive adsorption. One exemplary application of the invention is in biomass utilization for sugar production. It may also be used for other enzyme and lignocellulose systems. Specifically, the invention is applicable to reduce the inhibition of enzymatic hydrolysis by the unbound lignin in the aqueous enzyme-lignocellulose systems or by the lignin remained on the lignocellulose substrate (i.e., bound lignin, not necessarily chemically bound).

The invention has significant implications to simultaneous saccharification and combined fermentation (SSCombF) of the cellulose fraction (lignocellulose solid substrate) with the hemicelluloses sugar stream (pretreatment spent liquor or hydrolysate). Currently, this cannot be done because unbound (dissolved or suspended) lignin in the hemicellulose sugar stream can significantly inhibit enzymatic saccharifcation of cellulose. And this invention is also related to processes to eliminate or reduce washing of the cellulose fraction (pretreated lignocellulose solids), which is required currently before enzymatic saccharification to reduce unbound lignin content on cellulose solid substrate. In certain aspects of this invention, washing can be reduced if not eliminated. This saves a lot of fresh water usage in commercial settings. It also offers the potential to accomplish SSCombF of the cellulose fraction with the hemicelluloses sugar stream.

II. Process Flow Schemes

In certain aspects, the present invention makes the use of metal compounds, especially divalent metal compounds or ions, such as Mg(II), $Mg^{2+}$ or Ca(II), $Ca^{2+}$, as a means of absorbing lignin during the processing of cellulose-containing materials into biofuels. It has been found in the present invention that metal compounds or metal ions can bind to lignin and this binding prevents lignin from interfering with enzymatic cellulose hydrolysis, for example, mM concentrations of metal salts could be added to processed biomass material, such as wood fibers or pulps, at room temperature without heavy washing to remove lignin. Also it has been found that cellulosic hydrolysis occurred at higher levels in the treated experiment than seen when the materials was unwashed without treatment with metal ions.

The present invention develops several process schemes based on these discoveries. Referring to FIG. 1, there is shown a specific example of a process in accordance with embodiments of the present invention. Particularly biomass material 101 (especially lignocellulosic biomass), including any woody and/or non-woody biomass, may be subjected to one or more pretreatment methods or a pretreatment reactor 102 to improve the accessibility of cellulase to the biomass cellulose in enzymatic hydrolysis. Pretreatment may include any methods that may at least partially disrupt the fiber structure of the biomass material 101, such as chemical, biological, thermal, or a combination of any of three types of methods. Pretreatment medium 103 such as steam, air or pretreatment liquor like hot water may be added to the pretreatment reactor 102. Also there might be added pretreatment chemicals 104 such as sulfite and/or bisulfate as used in SPORL (sulfite pretreatment to overcome recalcitrance of lignocellulose) (see U.S. Publ. 2009/0298149, incorporated herein by reference). After pretreatment, there may be provided a mixture of solid material and liquid.

Optionally, the process may have a separation step 105. The separation step 105 may separate the pretreated solid-liquid mixture into a solid (e.g., the solid fraction containing cellulose and insoluble lignin) and a liquid fraction 110 (i.e., spent liquor or pretreatment hydrolysate) containing the dissolved ingredients (e.g., hemicellulose and a small amount of solubilized lignin). The separation methods may include any methods that separate solid from liquid, such as filtration, screening, or pressing.

A problem associated with the fermentation of hemicellulosic sugars to biofuel is the presence of a broad range of compounds, which can inhibit the fermenting microorganisms. The inhibitory or toxic compounds include hydroxymethylfurfural (HMF), furfural (compounds derived from hexoses and pentoses degradation, respectively), acetic acid (released from the hemicellulosic structure), and phenolics (formed from the partial degradation of lignin). These inhibitors can be removed from the hydrolysate 110 by a detoxification method 111 prior to fermentation 112 to produce biofuel 109. Detoxification methods may include neutralization, evaporation, and adsorption on activated charcoal, or ion-exchange resins.

The solid substrate may also be subjected to a size reduction step 106. The separation step 105 may be prior to or after the size reduction step 106. The size reduction step 106 may include any methods that reduce the size of a solid biomass material, such as milling, abrading, grinding, crushing, chopping, chipping or the like. The process may obviate a washing step, especially an independent washing step, which adds water and then removes water as well as residual chemicals and other components (such as dissolved lignin), because metal compounds 107 may be added to reduce lignin absorption of cellulase enzymes. Optionally, water may be added in the size reduction step 106 such as disk milling for minor washing and thus milling energy may be significantly reduced.

The cellulose molecules are composed of long chains of glucan. Hydrolysis may be used to break down these chains into individual sugars for biofuel production. For cellulose hydrolysis, there may be at least two major hydrolysis methods, including chemical hydrolysis and enzymatic hydrolysis. Enzymatic hydrolysis may hydrolyze cellulose at relatively mild conditions and have been widely used.

As described above, metal compounds 107 may be applied to the solid material, especially unwashed solid material, to enhance enzymatic hydrolysis by eliminating inhibitions of enzymes by lignin. For production of biofuel or other products 109, there may be provided several processes such as cellulosic substrate separate enzymatic hydrolysis (SHF) or simultaneous saccharification and fermentation (SSF) 108.

In SHF, the cellulose hydrolysis and fermentation are in separate reactors or separate steps. This may be advantageous because experiments may be carried out at the optimum conditions for hydrolysis and fermentation, respectively. However, the main disadvantage is that the sugars released in the hydrolysis can severely inhibit the forward hydrolysis reaction. In SSF, the saccharification (i.e., hydrolysis) of cellulose to glucose with cellulase and the subsequent fermentation of glucose (and/or pentose) to biofuel, ethanol and/or other byproducts take place in the same reactor or the same step. The advantages of SSF include enhanced rate of cellulose hydrolysis due to uptake of sugars to move the hydrolysis forward and decreased requirement of aseptic conditions.

Figure 2:
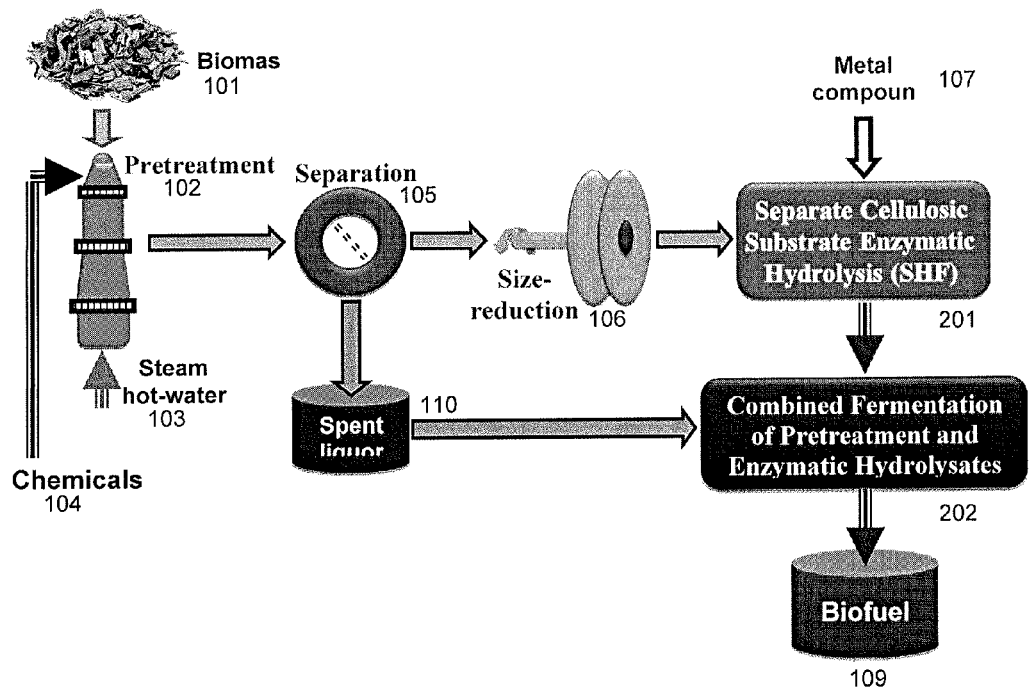
FIG. 2. Another exemplary embodiment of biofuel production process flow.

Referring to FIG. 2, there is shown another example of a process in accordance with embodiments of the present invention. Metal compound 107 may be applied to the solid material for separate cellulosic substrate enzymatic hydrolysis (SHF) 201. The resulting enzymatic hydrolysate and spent liquor (i.e., pretreatment hydrolysate) 110 may be combined or fed into the same reactor for an integrated process 202 such as combined fermentation of pretreatment and enzymatic hydrolysates or fed-batch fermentation. Detoxification 111 of pretreatment hydrolysates (e.g., hemi cellulosic sugar stream) 110 may be eliminated by the metal application into the spent liquor 110 via integration of processes.

Figure 3:
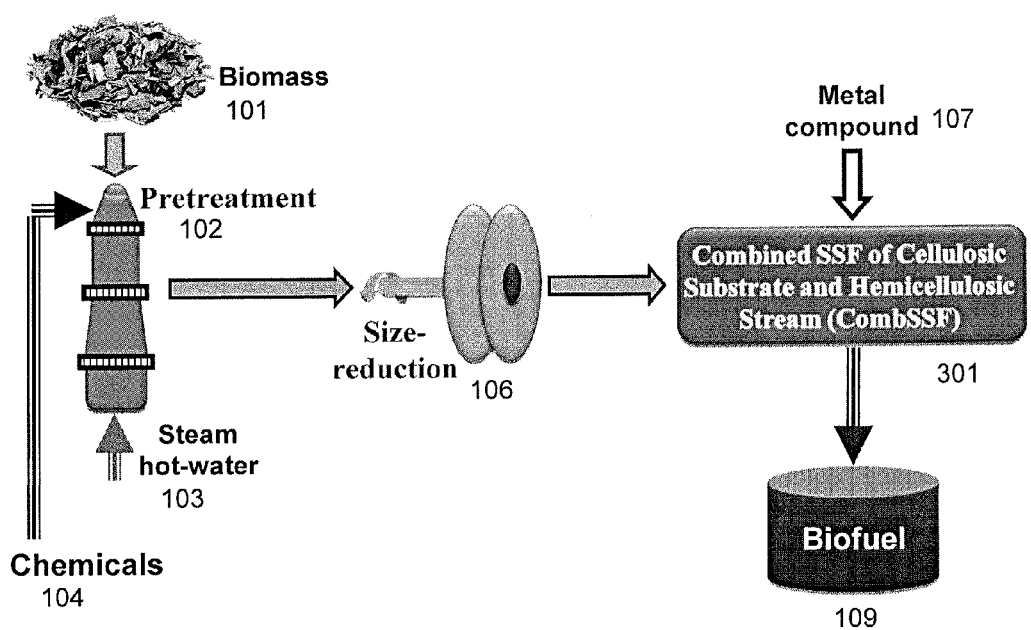
FIG. 3. Another exemplary embodiment of biofuel production process flow.

Referring to FIG. 3, there is shown a more simplified and efficient example of a process in accordance with embodiments of the present invention. Metal 107 may be applied for combined simultaneous saccharification and fermentation (CombSSF) 301 of the cellulosic solid substrate and pretreatment hydrolysate (or hemicellulosic sugar stream) to eliminate inhibition of enzymes by lignin or other compounds in the unwashed substrate. By preventing lignin inhibition and enhancing enzymatic hydrolysis, the separation step 105 may be eliminated.

Figure 27:
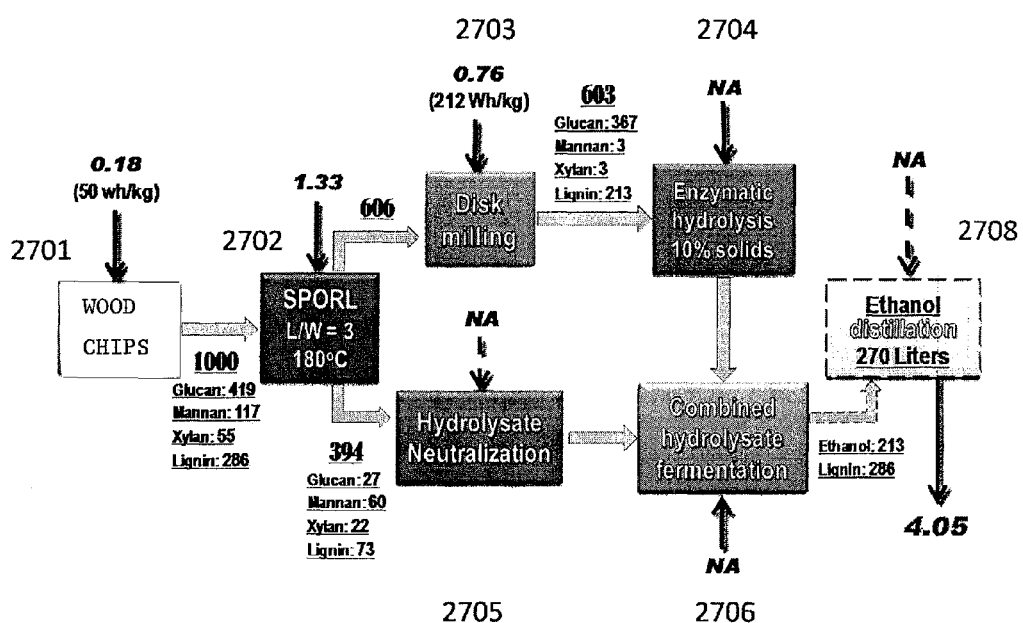
FIG. 27. Block diagram showing process mass and energy balance of the SSCombF experiment using $Ca(OH)_2$ neutralized hydrolysate. Unless indicated, energy data are in GJ/ton wood and mass data are in kilograms.
Figure 28:
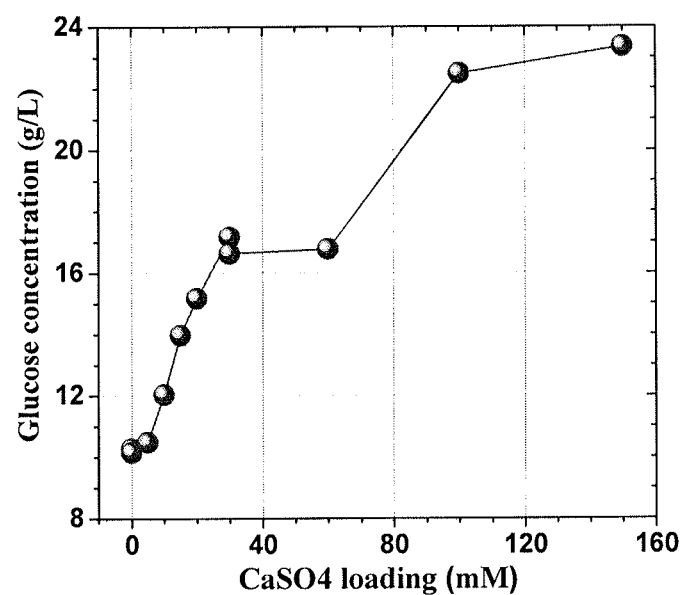
FIG. 28. The effect of $CaSO_4$ application dosage on measured glucose concentrations in an enzymatic hydrolysate of a unwashed SPORL-pretreated lodgepole pine solid substrate hydrolyzed at 10% solid consistency with cellulase loading of 9 FPU/g substrate and β-glucosidase 9 CBU/g substrate.

Referring to FIG. 27, there is shown an example of a simultaneous saccharification of lignocellulose and combined fermentation (SSCombF) process in accordance with embodiments of the present invention. Cellulosic material like wood chips 2701 may be subject to sulfite pretreatment methods such as SPORL 2702. After sulfite pretreatment 2702, the resulting slurry may be separated into a solid portion and a liquid portion (spent liquor or hydrolysate). The solid portion may be reduced in size by disk milling 2703, followed by enzymatic hydrolysis 2704 to produce enzymatic hydrolysate, which be partially hydrolyzed. The liquid portion of hydrolysate (pretreatment hydrolysate) may be added with metal, for example, conditioned using $Ca(OH)_2$ powder under simple neutralization to a pH of about or less than 7, such as pH 5, or alternatively overliming to a basic pH such as pH 10. The resulting enzymatic hydrolysate from 2704 and neutralized hydrolysate from 2705 may be combined or fed into the same reactor for an integrated process 2706 such as combined hydrolysis and fermentation of pretreatment and enzymatic hydrolysates (the enzymatic hydrolysate may continue to be hydrolyzed with the aid of metal compounds including metal ions). Detoxification of pretreatment hydrolysates (e.g., hemicellulosic sugar stream) may be eliminated by the metal application into the spent liquor in step 2705 via integration of processes.

III. Metal and Enzymatic Hydrolysis

In certain aspects, metal compounds, especially divalent metal compounds, may be used to improve enzymatic hydrolysis of biomass material. The metal compound may be used to prevent absorption of cellulase enzymes by lignin, therefore eliminating the need for the steps of lignin removal, such as washing or solid-liquid separation steps. Therefore, there may be provided methods of biomass processing including applying metal compounds to biomass material but without washing or separate steps.

Nonproductive adsorption of enzymes by compounds other than cellulose in enzyme and lignocellulose systems has been recognized as the major cause of loss of enzyme activity which results in reduced efficiency of cellulose hydrolysis (Eriksson et al. 2002; Mansfield et al. 1999; Yang and Wyman 2006; Zheng et al. 2008). Lignin may account for 20-30% of biomass and has been recognized as one of the key nonproductive enzyme adsorption medium (Mansfield, 1999). Research effort has been made to remove lignin content of lignocellulose substrate through delignification to reduce its inhibition on enzymatic hydrolysis (Pan et al. 2004). However, delignification operation is expensive. Furthermore, it only addresses the lignin on the solid lignocellulose substrate. It does not apply to the remaining unbound lignin attached to the solid lignocellulosic substrate even after washing. Exogenous protein (bovine serum albumin-BSA) has been used to covering lignin to reduce adsorption of cellulase onto lignin to enhance enzymatic cellulose saccharification (Pan et al. 2005; Yang and Wyman 2006; Zheng et al. 2008). Surfactants has also been used as lignin-block agents to improve enzymatic hydrolysis (Eriksson et al. 2002; Borjesson et al. 2007; Ooshima et al. 1990; Tu et al. 2009; Zheng et al. 2008). These two techniques have proven to be efficient to reduce nonproductive adsorption of enzymes by lignin. However, both of these two techniques have difficulties for commercial applications, for example, proteins are expensive. Surfactant may cause foaming that can be a significant disadvantage in simultaneous saccharification and fermentation of lignocellulosic solid substrate.

The adsorption properties of lignin-metal complex for enzymes have not been examined and reported. Part of the novelty of the present invention is the utilization of the formation of lignin-metal complex to reduce or eliminate nonproductive enzyme adsorption by lignin in enzyme-lignocellulose systems. Without wishing to be bound by theory, it is contemplated that certain metal compounds (including metal ions) can form complexes with lignin to deactivate adsorption of enzymes. These metal compounds (including metal ions) are not toxic to enzymes, such as Ca(II), $Ca^{2+}$ and Mg(II), $Mg^{2+}$. Therefore, these metal compounds can be used to enhance enzymatic hydrolysis of lignocelluloses substrate.

In certain aspects, divalent metal compounds, especially metal salts, may be mixed with solid-containing biomass material in an aqueous solution, especially unwashed and pretreated biomass material, prior to or during enzymatic hydrolysis. The metal compounds may reduce or eliminate nonproductive enzyme absorption by lignin, both bound and unbound to the solid (e.g., wood). The aqueous solution may be at a pH of 1, 2, 3, 4, 5, 6, 7, 8, 9, 10 or any range derivable therein. In particular, the pH may be about 2 to 8, or more particularly, about 4 to 7. For example, the divalent metal salt may comprise any metal salt of calcium or magnesium. In certain aspects, the solid material has lignin of about 0.1, 0.5, 1, 5, 10, 15, 20, 25, 30, 35, 40, 45, 50, 55, 60, 65, 70, 75, 80, 90, 95 percent or any intermediate ranges or numbers. For example, the solid material may have a lignin content of about 0.1 to 95%, more specifically, 5 to 50%. In further aspects, the divalent metal compound may be mixed with the solid material at about 0.01, 0.05, 0.1, 0.5, 1, 2, 3, 4, 5, 6, 7, 8, 9, 10, 20, 50 mol per kilogram solid material or any intermediate ranges or numbers. The mixing of solid material and the divalent metal compound may occur at a temperature of about 5, 10, 15, 20, 25, 30, 37, 40, 45, 50, 55, 60, 65, 70, 75° C. or any range derivable therein.

IV. Modification of Washing Step

A washing step for removal of unbound lignin as used in conventional biomass process may be water and energy intensive. In particular embodiments of the invention, the washing step may be eliminated because the beneficial effect of metal compound on lignin inhibition.

It is well known that lignin can inhibit enzymatic hydrolysis of cellulose through nonproductive adsorption (Mansfield et al., 1999; Sewalt et al., 1997; Tengborg et al., 2001). The removal of the inhibitions by unbound lignin (here refers to lignin in pretreatment hydrolysate free from wood) and other impurities in pretreatment hydrolysate/spent liquor were commonly achieved by washing the lignocellulosic substrate before enzymatic hydrolysis (Nagle et al., 2002; Sinitsyn et al., 1982; Tengborg et al., 2001). Because the unbound lignin after an acidic type pretreatment tends to condense and precipitate, a pressurized hot washing process was also developed for further removal of lignin and hemicelluloses (Nagle et al., 2002). However, substrate washing can consume a significant amount of water for commercial cellulosic ethanol production with a typical capacity of 2000 ton biomass/day (a typical pulp mill with similar capacity uses about 10,000 $m^3$/day water for pulp washing), which would be a great environmental concern. Furthermore, high temperature/pressure washing is energy intensive. The significant dilution incurred from washing also requires an energy intensive concentration step to reclaim the hemicelluloses sugars in the washing filtrate. Moreover, the inhibition of enzymatic cellulose hydrolysis by the unbound lignin dissolved in the pretreatment hydrolysate can prevent practicing simultaneous saccharification of lignocellulose and combined fermentation (SSCombF) of the cellulosic fraction with the hemicellulosic sugar stream. The benefits of SSCombF, which include simplifying the production process and alleviating end-product inhibition of enzymes at high carbohydrate loadings, may be overweighed by the nonproductive adsorption of enzymes by unbound lignin. Therefore, addressing the inhibition of enzymatic hydrolysis of lignocelluloses by unbound lignin has significant importance for practical applications.

There are several possible alternatives to washing to improve enzymatic hydrolysis of lignocelluloses. Excess cellulase loading in hydrolysis is one solution but at the expense of increasing enzyme cost. Using additives, such as bovine serum albumin (BSA) and surfactants, to "block" lignin from interacting with cellulase has proven effective (Borjesson et al., 2007; Eriksson et al., 2002; Pan et al., 2005; Tu et al., 2009; Yang & Wyman, 2006; Zheng et al., 2008). However BSA is too expensive to be economically feasible for commercial biorefineries. Surfactants application at the dosage of about 0.2%, as commonly used in the literature, may negatively affect downstream processing and can also be expensive.

As discovered in certain aspects of the present invention, the application of certain metal compounds and ions, such as Ca(II), $Ca^{2+}$ and Mg(II), $Mg^{2+}$ was found to enhance enzymatic hydrolysis of pure cellulose spiked with lignin, i.e., lignosulfonate, kraft lignin, and Organosolv lignin. It is known that certain metal compounds can associate with lignin (Torre et al., 1992). It has been contemplated herein that the formation of lignin-metal complexes (liming or overliming of pretreatment hydrolysate may produce similar phenomena of lignin-Ca(II) complexation) may play a role in reducing affinity of lignin to cellulase enzymes.

As shown in Examples, metal salts may be applied to unwashed pretreated lignocellulosic substrate containing unbound (can be dissolved) lignosulfonate. Different metal salts may be first applied to a pure cellulose system spiked with purified lignosulfonate from SPORL (sulfite pretreatment to overcome recalcitrance of lignocelluloses) of eucalyptus. Then metal salts may be applied to unwashed and washed aspen substrate from SPORL. It has been demonstrated that the application of metal salts could enhance enzymatic hydrolysis of unwashed pretreated lignocellulose.

Therefore, one embodiment of the invention is to eliminate substrate washing to save water or reduce enzyme loading while achieving efficient enzymatic saccharification using inexpensive metal salts. In certain aspects that washing may be included but at a lower dosage and energy cost, the substrate washing may be performed at a temperature of less than 50° C., especially about or up to 20, 25, 30, 35, 40, 45° C., or any intermediate numbers or ranges.

V. Pretreatment

In certain aspects, pretreatment methods may be used to make cellulose more accessible to saccharification, in combination with the metal application as described above. In a particular embodiment, there may be provided a method comprising SPORL pretreatment followed by metal treatment of lignin-containing biomass material.

Although lignocellulose is the most abundant plant material resource, its susceptibility to enzyme processing has been curtailed by its rigid structure. As the result, an effective pretreatment is included to liberate the cellulose from the lignin seal and its crystalline structure so as to render it accessible for a subsequent enzymatic hydrolysis step. By far, most pretreatments are done through physical or chemical means. In order to achieve higher efficiency, there may be provided pretreatment methods in combination with the metal application, such as physical and chemical pretreatment methods. Physical pretreatment is often called size reduction to reduce biomass physical size. Chemical pretreatment is to remove chemical barriers so that the enzymes can access to cellulose for microbial destruction.

To date, the available pretreatment techniques include acid hydrolysis, steam explosion, ammonia fiber expansion, Organosolv, sulfite pretreatment to overcome recalcitrance of lignocellulose (SPORL) (Pan et al., 2005; Zhu et al., 2009) alkaline wet oxidation and ozone pretreatment (Torre et al., 1992). Besides effective cellulose liberation, an ideal pretreatment has to minimize the formation of degradation products because of their inhibitory effects on subsequent hydrolysis and fermentation processes (Guo et al., 2008). The presence of inhibitors will not only further complicate the ethanol production but also increase the cost of production due to entailed detoxification steps. Even though pretreatment by acid hydrolysis is probably the oldest and most studied pretreatment technique, it produces several potent inhibitors including furfural and hydroxymethyl furfural (HMF) which are by far regarded as the most toxic inhibitors present in lignocellulosic hydrolysate (Crist et al., 2003). Ammonia Fiber Expansion (AFEX) is a promising pretreatment with no inhibitory effect in resulting hydrolysate Varma et al., 1989) but is not effective on woody biomass.

Most pretreatment processes are not effective when applied to feedstocks with high lignin content, such as forest biomass. Organosolv and SPORL (Zhu et al., 2009) (also see U.S. Publ. 2009/0298149, incorporated herein by reference) are two processes that can achieve over 90% cellulose conversion for forest biomass, especially those of softwood species. SPORL is the most energy efficient (sugar production per unit energy consumption in pretreatment) and robust process for pretreatment of forest biomass with very low production of fermentation inhibitors (Zhu et al., 2010).

VI. Enzymatic Hydrolysis

In certain embodiments, an aqueous composition containing the metal-treated solid material may be contacted with one or more cellulase enzymes, at a pH and a temperature sufficient to produce a saccharification product. As used herein, the term "saccharification" refers to the hydrolysis of polysaccharides to their constituent monomers and/or oligomers. As used herein, the term "cellulase" refers to polysaccharide-hydrolyzing enzymes that can exhibit an activity, such as cellulose degradation, that may be several enzymes or a group of enzymes having different substrate specificities. Thus, a cellulase from a microorganism may comprise a group of enzymes, all of which may contribute to the cellulose-degrading activity.

Prior to saccharification, the aqueous composition may be treated to alter the pH, composition or temperature such that the cellulase enzyme(s) will be active. The pH may be altered through the addition of alkalis or acids in solid or liquid form. Alternatively, carbon dioxide ($CO_2$), which may be recovered from fermentation, may be utilized to lower the pH. For example, $CO_2$ may be collected from a fermenter and fed, such as by bubbling, into the aqueous suspension of the solid while monitoring the pH, until the desired pH is achieved.

Buffer may also be added to maintain the desired pH. The temperature may be brought to a temperature that is compatible with cellulase enzyme activity, as noted below. Any cofactors required for activity of enzymes used in saccharification may be added.

The solid material may be then further hydrolyzed in the presence of one or more saccharification enzymes such as cellulase enzymes to release oligosaccharides and/or monosaccharides in a hydrolyzate. Saccharification enzymes and methods for biomass treatment are reviewed in Lynd et al. (2002).

The saccharification enzyme comprises one or more enzymes selected primarily, but not exclusively, from the group "glycosidases" which hydrolyze the ether linkages of di-, oligo-, and polysaccharides and are found in the enzyme classification EC 3.2.1.x (Enzyme Nomenclature 1992, Academic Press, San Diego, Calif. with Supplement 1 (1993), Supplement 2 (1994), Supplement 3 (1995, Supplement 4 (1997) and Supplement 5 [in Eur. J. Biochem. (1994), Eur. J. Biochem. (1995), Eur. J. Biochem. (1996), Eur. J. Biochem. (1997), and Eur. J. Biochem. (1999), respectively]) of the general group "hydrolases" (EC 3.). Glycosidases useful in the present method can be categorized by the biomass component that they hydrolyze. Glycosidases useful for the present method include cellulose-hydrolyzing glycosidases (for example, cellulases such as endoglucanases, exoglucanases, (β-glucosidases, or cellobiohydrolases), hemicellulose-hydrolyzing glycosidases (for example, xylanases, endoxylanases, exoxylanases, β-xylosidases, arabinoxylanases, mannases, galactases, pectinases, glucuronidases), and starch-hydrolyzing glycosidases (for example, amylases, α-amylases, β-amylases, glucoamylases, α-glucosidases, isoamylases). In addition, it may be useful to add other activities to the saccharification enzyme such as peptidases (EC 3.4.x.y), lipases (EC 3.1.1.x and 3.1.4.x), ligninases (EC 1.11.1.x), and feruloyl esterases (EC 3.1.1.73) to help release polysaccharides from other components of the biomass.

It is well known in the art that microorganisms that produce polysaccharide-hydrolyzing enzymes often exhibit an activity, such as cellulose degradation, that is catalyzed by several enzymes or a group of enzymes having different substrate specificities. Thus, a "cellulase" from a microorganism may comprise a group of enzymes, all of which may contribute to the cellulose-degrading activity. Commercial or non-commercial enzyme preparations, such as cellulase, may comprise numerous enzymes depending on the purification scheme utilized to obtain the enzyme. Thus, the saccharification enzymes of the present method may comprise enzyme activity, such as "cellulase," however it is recognized that this activity may be catalyzed by more than one enzyme.

Saccharification enzymes may be obtained commercially, such as Spezyme® CP cellulase (Genencor International, Rochester, N.Y.) and Multifect® xylanase (Genencor). In addition, saccharification enzymes may be produced biologically, including using recombinant microorganisms.

Particularly the saccharification reaction is performed at or near the temperature and pH optima for the saccharification enzymes. The temperature optimum used with the saccharification enzyme in the present method may range from about 15° C. to about 100° C. The temperature optimum may range from about 20° C. to about 80° C., or from about 30° C. to about 60° C., or from about 45° C. to about 55° C. The pH optimum may range from about 4 to about 6 or from about 4.5 to about 5.7.

The saccharification may be performed for a time of about several hours to a few days, for example from about 2 hours to about 3 days. The time for the reaction may depend on enzyme concentration and specific activity, as well as the substrate used and the environmental conditions, such as temperature and pH. One skilled in the art can readily determine optimal conditions of temperature, pH and time to be used with a particular substrate and saccharification enzyme(s). These variables may be adjusted as necessary to obtain an optimal saccharification product for use in fermentation.

The saccharification may be performed batch-wise or as a continuous process. The saccharification may also be performed in one step, or in a number of steps. For example, different enzymes required for saccharification may exhibit different pH or temperature optima. A primary treatment can be performed with enzyme(s) at one temperature and pH, followed by secondary or tertiary (or more) treatments with different enzyme(s) at different temperatures and/or pH. In addition, treatment with different enzymes in sequential steps may be at the same pH and/or temperature, or different pHs and temperatures, such as using hemicellulases stable and more active at higher pHs and temperatures followed by cellulases that are active at lower pHs and temperatures.

The saccharification reaction may be performed in any suitable vessel, such as a batch reactor a continuous reactor. The suitable vessel may be equipped with a means, such as impellers, for agitating the biomass/acid mixture. Reactor design is discussed in Lin and Van Ness, 1973).

The degree of solubilization of sugars from biomass following saccharification may be monitored by measuring the release of monosaccharides and oligosaccharides. Methods to measure monosaccharides and oligosaccharides are well known in the art. For example, the concentration of reducing sugars can be determined using the 1,3-dinitrosalicylic (DNS) acid assay (Miller, 1959). Alternatively, sugars can be measured by HPLC using an appropriate column as described herein in the General Methods section.

VII. Production of Biofuel or Other End Products

In certain aspects of the invention, biofuel like ethanol or other end products may be produced from metal-treated biomass material by microbial fermentation. During fermentation, both C5 and C6 sugars are fermented to ethanol under anaerobic/aerobic conditions. Historically, yeast (*Saccharomyces cerevisiae*) was used to ferment C6 sugars, i.e., glucose. Similarly, other microbes like *Zymomonas mobilis* have also been used. Other engineered microbes like *Escherichhia coli* have also been developed which can ferment both C6 and C5 sugars.

Based on the different combinations of technologies adopted at the pretreatment, hydrolysis, and fermentation stages of ethanol synthesis, several integrated technologies have been developed.

A. End Products

The readily saccharifiable biomass produced by the present methods may be hydrolyzed by enzymes as described above to produce fermentable sugars which then may be fermented into biofuel or other end products. "Fermentation" refers to any fermentation process or any process comprising a fermentation step. End products include, without limitation alcohols (e.g., arabinitol, butanol, ethanol, glycerol, methanol, 1,3-propanediol, sorbitol, and xylitol); organic acids (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, and xylonic acid); ketones (e.g., acetone); amino acids (e.g., aspartic acid, glutamic acid, glycine, lysine, serine, and threonine); gases (e.g., methane, hydrogen ($H_2$), carbon dioxide ($CO_2$), and carbon monoxide (CO)).

Fermentation processes also include processes used in the consumable alcohol industry (e.g., beer and wine), dairy industry (e.g., fermented dairy products), leather industry, and tobacco industry.

Further to the above, the sugars produced from saccharifying the pretreated biomass as described herein may be used to produce in general, organic products, chemicals, fuels, commodity and specialty chemicals such as xylose, acetone, acetate, glycine, lysine, organic acids (e.g., lactic acid), 1,3-propanediol, butanediol, glycerol, ethylene glycol, furfural, polyhydroxyalkanoates, cis, cis-muconic acid, and animal feed (Lynd et al., 1999; and Philippidis, 1996; and Ryu and Mandels, 1980).

Potential coproducts may also be produced, such as multiple organic products from fermentable carbohydrate. Lignin-rich residues remaining after pretreatment and fermentation may be converted to lignin-derived chemicals, chemical building blocks or used for power production.

B. Microbial Fermentation

Traditionally, baker's yeast (*Saccharomyces cerevisiae*) has long been used in the brewery industry to produce ethanol from hexoses (6-carbon sugar). Due to the complex nature of the carbohydrates present in lignocellulosic biomass, a significant amount of xylose and arabinose (5-carbon sugars derived from the hemicellulose portion of the lignocellulose) is also present in the hydrolysate. For example, in the hydrolysate of corn stover, approximately 30% of the total fermentable sugars is xylose. As a result, the ability of the fermenting microorganisms to use the whole range of sugars available from the hydrolysate is vital to increase the economic competitiveness of cellulosic ethanol and potentially bio-based chemicals.

In recent years, metabolic engineering for microorganisms used in fuel ethanol production has shown significant progress (Pan et al., 2006). Besides *Saccharomyces cerevisiae*, microorganisms such as *Zymomonas mobilis* and *Escherichia coli* have been targeted through metabolic engineering for cellulosic ethanol production.

Recently, engineered yeasts have been described efficiently fermenting xylose (Davis, 1998; Salmon, 1991) and arabinose (Bhardwaj et al., 2004), and even both together (Katz et al., 1984). Yeast cells are especially attractive for cellulosic ethanol processes as they have been used in biotechnology for hundreds of years, as they are tolerant to high ethanol and inhibitor concentrations and as they can grow at low pH values which avoids bacterial contaminations.

C. Combined Hydrolysis and Fermentation

Some species of bacteria have been found capable of direct conversion of a cellulose substrate into ethanol. One example is *Clostridium thermocellum*, which uses a complex cellulosome to break down cellulose and synthesize ethanol. However, *C. thermocellum* also produces other products during cellulose metabolism, including acetate and lactate, in addition to ethanol, lowering the efficiency of the process. Some research efforts are directed to optimizing ethanol production by genetically engineering bacteria that focus on the ethanol-producing pathway.

Conventional methods of fermentation and/or saccharification are known in the art including, but not limited to, saccharification, fermentation, separate hydrolysis and fermentation (SHF), simultaneous saccharification and fermentation (SSF), simultaneous saccharification and cofermentation (SSCF), hybrid hydrolysis and fermentation (HHF), and direct microbial conversion (DMC).

SHF uses separate process steps to first enzymatically hydrolyze cellulose to sugars such as glucose and xylose and then ferment the sugars to ethanol. In SSF, the enzymatic hydrolysis of cellulose and the fermentation of glucose to ethanol is combined in one step (Philippidis, 1996). SSCF includes the cofermentation of multiple sugars (Sheehan and Himmel, 1999). HHF includes two separate steps carried out in the same reactor but at different temperatures, i.e., high temperature enzymatic saccharification followed by SSF at a lower temperature that the fermentation strain can tolerate. DMC combines all three processes (cellulase production, cellulose hydrolysis, and fermentation) in one step (Lynd et al., 2002).

These processes may be used to produce end products like biofuel from the readily saccharifiable biomass produced by the metal treatment methods described herein.

VIII. Biomass Material

In certain aspects of the present invention, biomass material may be used as substrate for the metal-aided saccharification and/or fermentation. In the biomass material, the carbohydrate polymers (cellulose and hemicelluloses) may be tightly bound to the lignin.

Cellulose, which is a β-glucan built up of anhydro D-glucose units, is the main structural component of plant cell walls and normally constitutes about 35-60% by weight (% w/w) of lignocellulosic materials.

Hemicellulose is the term used to denote non-cellulosic polysaccharides associated with cellulose in plant tissues. Hemicellulose frequently constitutes about 20-35% w/w of lignocellulosic materials, and the majority of hemicelluloses consists of polymers based on pentose (five-carbon) sugar units, such as D-xylose and D-arabinose units, and hexose (six-carbon) sugar units, such as D-glucose, D-mannose and D-galactose units. Generally, hardwood hemicellulose contains more xylose and softwood hemicellulose more mannose.

Lignin, which is a complex, cross-linked polymer based on variously substituted hydroxyphenylpropane units, generally constitutes about 10-30% w/w of lignocellulosic materials. It is believed that lignin functions as a physical barrier to the direct bioconversion (e.g., by cellulase) of cellulose and hemicellulose in lignocellulosic materials which have not been subjected to some kind of pre-treatment process (which may very suitably be the SPORL process as described in relation to the present invention) to disrupt the structure of lignocellulose.

The biomass material may be wood, such as hardwood and softwood, or herbaceous feedstock. Biomass refers to living and recently dead biological material that can be used as fuel or for industrial production. Most commonly, biomass refers to plant matter grown for use as biofuel, but it also includes plant or animal matter used for production of fibers, chemicals or heat. Biomass may also include biodegradable wastes that can be burnt as fuel. In certain embodiments, biomass may be grown crop fiber consisting primarily of cellulose, hemicellulose and lignin, and includes, without limitation, grass, switchgrass, straw, corn stover, cane residuals, general cereal wastes, wood chips and the like, that can be converted to ethanol (or other products) according to U.S. Pat. No. 4,461,648 and U.S. Pat. No. 5,916,780, or other known technology.

A. Hardwood

Hardwood comprises wood from broad-leaved (mostly deciduous, but not necessarily, in the case of tropical trees) or angiosperm trees. On average, hardwood is of higher density and hardness than softwood, but there is considerable variation in actual wood hardness in both groups, with a large amount of overlap; some hardwoods (e.g., balsa) are softer than most softwoods, while yew is an example of a hard softwood. Hardwoods may have broad leaves and enclosed nuts or seeds such as acorns. They may grow in subtropical regions like Africa and also in Europe and other regions such as Asia. The dominant feature separating hardwoods from softwoods is the presence of pores, or vessels. Examples of hardwood are described in U.S. Publ. 2009/0298149 (incorporated herein by reference).

B. Softwood

Softwood is a generic term used in woodworking and the lumber industries for wood from conifers (needle-bearing trees from the order Pinales). Softwood-producing trees include pine, spruce, cedar, fir, larch, douglas-fir, hemlock, cypress, redwood and yew. Softwood is also known as Clarkwood, Madmanwood, or fuchwood. Examples of softwood are described in U.S. Publ. 2009/0298149 (incorporated herein by reference).

C. Biomass Feedstock

Biomass feedstock comes in many different types, such as wood residues (including sawmill and paper mill discards), municipal paper waste, agricultural residues (including corn stover, straw, hull and sugarcane bagasse), and dedicated energy crops, which are mostly composed of fast growing tall, woody biomass.

Corn stover comprises leaves and stalks of maize (*Zea mays* ssp. *mays* L.) plants left in a field after harvest. It makes up about half of the yield of a crop and is similar to straw, the residue left in field after harvest of any cereal grain. It can be used as a fuel for bioenergy or as feedstock for bioproducts. Maize stover, together with other cellulosic biomass, provides about the potential 1.3 billion tons of raw materials per year that could produce future fuel in the next 50 years.

Useful sources of straw include in particular cereals (cereal grasses), i.e., gramineous plants which yield edible grain or seed. Straw from, for example, oat (*Avena* spp., such as *A. saliva*), barley (*Hordeum* spp., such as *H. vulgare*), wheat (*Triticum* spp., including *T. durum*), rye (*Secal cereale*), rice (*Oryza* spp.), millet (e.g., species of *Digitaria, Panicum, Paspalism, Pennisetum* or *Setana*), sorghum (*Sorghum* spp., including *S. bicolor* var. *durra* (also referred to as "durra") and milo), buckwheat (*Fagopyrum* spp., such as *F. esculentum*) and maize (also referred to as corn (*Zea mays*), including sweetcorn) is well suited for treatment according to the process of the invention.

As employed herein, the term "hull" generally denotes the outer covering, rind, shell, pod or husk of any fruit or seed, but the term as employed herein also embraces, for example, the outer covering of an ear of maize. Relevant hulls include hulls selected among the following: hulls from oat (*Avena* spp., such as *A. saliva*), barley (*Hordeum* spp., such as *H. vulgare*), wheat (*Triticum* spp., including *T. durum*), rye (*Secal cereale*), rice (*Oryza* spp.), millet (e.g., species of *Digiftaa, Panicum, Paspalum, Pennisetum* or *Setaria*), sorghum (*Sorghum* spp., including *S. bicolor* var. durra and milo), buckwheat (*Fagopyrum* spp., such as *F. esculentum*), maize (also known as corn (*Zea mays*), including sweetcorn), corn cob, rape-seed (from *Brassica* spp., such as *B. napus, B. napus* subsp. *rapifera* or *B. napus* subsp. *oleifera*), cotton-seed (from *Gossypium* spp., such as *G. heraceum*), almond (*Prunus dulcis*, including both sweet and bitter almond) and sunflower seed (*Helianthus* spp., such as *H. annuus*).

Hulls of cereals, including not only those mentioned among the above, but also hulls of cereals other than those mentioned among the above, are generally of interest in the context of the invention, and particular hulls, such as oat hulls and barley hulls, belong to this category. In this connection it may be mentioned by way of example that oat hulls are often available in large quantities at low cost as a by-product of oat-processing procedures for the production of oatmeal, porridge oats, rolled oats and the like; thus, a total of around 75,000 tons of oat hulls is produced per year as a by-product of oat-processing in Denmark, Norway and Sweden together with northern Germany. Other types of hulls of relevance in relation to processes of the invention include, for example, palm shells, peanut shells, coconut shells, other types of nut shells, and coconut husk.

It should be noted that the native physical form, bulk and/or dimensions of cellulosic materials such as wood, straw, hay and the like will generally necessitate, or at least make it desirable, to carry out size reduction of the material (e.g., by milling, abrading, grinding, crushing, chopping, chipping or the like) to some extent in order to obtain particles, pieces, fibers, strands, wafers, flakes or the like of material of sufficiently small size and/or sufficiently high surface area to mass ratio to enable degradation of the material to be performed satisfactorily. In the case of wood, material of suitable dimensions will often be available as a waste product in the form of sawdust, wood chips, wood flakes, twigs and the like from sawmills, forestry and other commercial sources.

In contrast, numerous types of hulls, e.g., cereal grain or seed hulls in general, including oat hulls as employed in the working examples reported herein, have in their native form sufficiently small dimensions and a sufficiently high surface area to mass ratio to enable them to be used directly, as cellulosic materials in a process according to the present invention.

IX. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Materials.

Two types of solid substrates were used in Examples 2-5: pure cellulose and lignocelluloses from pretreated eucalyptus wood. Whatman Quantitative Filter Paper (Grade No. 41, Whatman, England; ash content <0.01) was defibrated for 8000 revolutions using a disintegrator (TMI, Ronkonkoma, N.Y.) to produce pure cellulosic substrate. Eucalyptus wood chips were screened to remove particles smaller than 6 mm and larger than 38 mm. The accepted wood chips have thickness ranging from 3-8 mm and were subjected to hot-water, dilute-acid, and two SPORL (Sulfite Pretreatment to Overcome Recalcitrance of Lignocellulose) pretreatments and then disk-milled to produce lignocellulosic solid substrates as described in the previous studies (Zhu et al., 2009; Zhu et al., 2010). All pretreatments were conducted at 180° C. with a liquid to wood ratio (L/W) of 3 for a fixed pretreatment duration time of 30 min. An extensive washing using deionized water was applied to milled fibrous substrates after disk milling to remove unbound lignin and other soluble substances adsorbed to the substrates. The major chemical components of the substrates were analyzed (Table 1). The lignin data includes both bound and the remaining (after washing) unbound lignin.

wood (L/W) ratio of 3 and acid and bisulfite charge on oven dry (od) wood of 1.1 and 3%, respectively, as described elsewhere (Zhu et al., 2010). At the completion of SPORL, the remaining solids remained as wood chips and were separated from spent liquor (pretreatment hydrolysate) using filter paper (Whatman No. 1, Whatman, England). The separated wood chips were directly fed into a disk mill (Andritz Sprout-

TABLE 1

Pretreatment conditions and chemical analysis results of the substrates

| | Agents[a] | | | | | | Substrate | Acid groups | |
| | Sulfuric | Sodium | Composition of substrates (%) | | | | solids | —$SO_3H$ | —COOH |
| Pretreatment | acid (%) | bisulfite (%) | Glucan | Xylan | Galactan | Lignin | yield (%) | µmol/g | µmol/g |
|---|---|---|---|---|---|---|---|---|---|
| Untreated wood | | | 41.8 | 10.4 | 1.8 | 28.5 | 100.0 | | |
| Hot-water | 0 | 0 | 53.5 | 2.3 | 0.2 | 37.2 | 76.0 | 0 | 112 |
| Dilute-acid | 1.1 | 0 | 55.6 | 0.6 | ND | 40.6 | 71.2 | 0 | 123 |
| SPORL high pH | 0 | 4 | 56.7 | 1.5 | ND | 33.8 | 69.8 | 24 | 113 |
| SPORL low pH | 1.1 | 4 | 56.3 | 0.3 | ND | 36.6 | 67.6 | 11 | 136 |
| Relative standard deviation (%) | | | 1.3 | 4.6 | 5.7 | 0.7 | | 2.5 | 6.0 |

[a]on oven dry (od) wood base in w/w

The cellulase complex used was a mixture of Cytolase CL preparation (Genencor, Menlo Park, Calif.) and (β-glucosidase (Novozyme 188) from commercial source (Sigma-Aldrich, St. Louis, Mo.). The enzyme activities of 43 FPU/mL for Cytolase CL and 415 CBU/mL for Novozyme 188 were calibrated using a method from the literature (Wood and Bhat, 1988).

$CaCl_2$, $CuCl_2$, $MgSO_4$, and $FeCl_3$ were all of analytical grade from a commercial source (Sigma-Aldrich, St. Louis, Mo.). High purity sulfonated lignin (SL) D748 from softwood sulfite pulping was donated by LignoTech USA (Rothschild, Wis.). Organosolv lignin (OL) was purchased from Sigma-Aldrich (St. Louis, Mo.). Kraft lignin (KL) was kindly provided by S. Ralph of the U.S. Forest Service, Forest Products Laboratory (Madison, Wis.). The SL and OL resemble the dissolved lignin in the pretreatment hydrolysates by SPORL and Organosolv pretreatments, respectively. These two pretreatments are the only two methods proven to produce excellent cellulose digestibility from woody biomass, especially softwood species. SL is water soluble and was directly added into cellulose suspension during experiments. OL and KL were dissolved in dilute NaOH solutions (pH 12) separately to make lignin solutions with concentration of 10 g/L for hydrolysis experiments. This is to better simulate enzymatic hydrolysis of unwashed lignocelluloses with unbound lignin. No pH changes were observed when OL and KL solution were added up to concentration of 0.1 g/L. However, when OL or KL lignin concentration was increased to 0.2 and 0.4 g/L, the measured pH was increased slightly by 0.04 and 0.09, respectively. About 20 and 50 µL HCl (1 M) was added, respectively, to adjust the pH back to 4.8±0.01.

Two types of cellulosic substrates were used in Examples 6-10. A pure cellulosic substrate was obtained by disintegrating commercial filter papers (Adventec No. 1, ADVANTEC, Japan) using a disintegrator (TMI, Ronkonkoma, N.Y.) for 8000 revolutions. A lignocellulosic substrate was produced from aspen wood chips using Sulfite Pretreatment to Overcome Recalcitrance of Lignocellulose (SPORL) (Wang et al., 2009; Zhu et al., 2009). The SPORL solution was made of dilute sodium bisulfite and sulfuric acid. The pretreatment was conducted in a 1 liter wood pulping digester using 150 g oven dry (od) wood at 170° C. for 25 min with a liquor to Bauer Atmospheric Refiner with disk-plate pattern D2-B505, Springfield, Ohio) without washing to produce lignocellulosic substrate.

Cellulase enzyme Multifect CL and Novozyme 188 (β-glucosidase) were purchased from Genencor (San Francisco, Calif.) and Sigma-Aldrich (St. Louis, Mo.), respectively. The enzyme activities were 73 FPU/mL and 413 CBU/mL for Multifect CL and Novozyme 188, respectively, determined following the International Union of Pure and Applied Chemistry (IUPAC) recommended method (Ghose, 1987). Soluble lignosulfonates were purified from in house produced SPORL hydrolysate using an Amicon ultrafiltration unit (Amicon, Beverly, Mass.) with a cut-off from 3 to 10 kDa. The pretreatment hydrolysate was produced from eucalyptus using SPORL at 180° C. with liquid to wood ratio of 3 and sulfuric acid and sodium bisulfite charge on wood (od) 1.1 and 4%, respectively. No carbohydrate was detected in the purified lignosulfonates samples by anion exchange chromatography described in the Analytical Methods section. Standard grade BSA was purchased from Sera Care (Milford, Mass.). All other chemicals were from commercial sources and of analytical grade.

Enzymatic Hydrolysis of Cellulosic Substrate.

For Examples 2-5, enzymatic hydrolysis of the cellulosic substrate was conducted at 1% solids concentration (w/v) in 50 mM acetate buffer (pH 4.8). After the addition of lignin or/and metal compound, the reaction flasks were incubated at 50° C. on the rotary shaker at 200 rpm for 15 min. Then the enzymes were added to start hydrolysis. The enzyme loadings were 15 and 7.5 FPU/g substrate for pure cellulose and pretreated wood substrates, respectively. The ratio of cellulase and β-glucosidase loading was 1:1. The pretreated substrates have cellulose contents from 42-57% (Table 1), therefore enzyme loading on a cellulose base is in the range of 13-18 FPU/g cellulose, similar to that for the pure cellulose substrate and those in the literature (Zhu et al., 2010; Pan et al., 2006). It was found that the pH of the aqueous cellulose-enzyme suspension was not affected by the addition of either SL or/and metal compounds. Aliquots of 300 µL were taken at different time points (1, 2, 4, 6, 12, 24, 36, and 48 h), and immediately heated in boiling water bath to stop enzymatic hydrolysis. The samples were then centrifuged at 4000 g for 5 min before glucose analysis. Control experiments were carried out without the addition of lignin and metal compound. Replicating hydrolysis experiments were conducted. The relative standard deviation of 2.5% determined from replicate measurements was used to determine error bars.

For Examples 6-10, enzymatic hydrolysis was performed in batch at 50° C. and pH 4.8 in an Erlenmeyer flask on a rotator incubator (Excella E25, New Brunswick Scientific Co., Edison, N.J.) at 200 rpm. Unless specified, the loading of Multifect CL was 5.0 and 10 FPU/g od substrate the SPORL aspen and filter paper cellulose, respectively. The loading ratio of Multifect CL to Novozyme 188 was kept at 1:1. The hydrolysis was conducted at 1% solids consistency (w/v), i.e., 1 od g substrate in 100 mL enzyme/buffer solution, for all substrates of pure cellulose, washed and unwashed aspen substrates from SPORL. Enzymatic hydrolysate was sampled periodically to obtain time-dependent glucose concentration. For each sampling point, a duplicate 0.4 mL suspension was taken for analysis. Duplicate hydrolysis experiments were conducted and the standard deviations were used as measurement errors. Error bars were omitted in some plots for clarity.

Analytical Methods.

The chemical composition of the unwashed and washed (at 25 and 98° C.) solid aspen lignocellulosic substrates or the original and pretreated solid substrates were determined by the Analytical and Microscopy Laboratory (USDA Forest Products Laboratory, Madison, Wis.). The substrates were first dried and then Wiley milled to a size passing a 20 mesh (~1 mm) screen. The resulting materials were hydrolyzed using sulfuric acid in two stages as described elsewhere (Zhu et al., 2010). The carbohydrates in the hydrolysate were analyzed using an improved high performance anion exchange chromatography with pulsed amperometric detection (HPAEC-PAD) (Davis, 1998). For fast analysis, the glucose in the enzymatic hydrolysates was measured using a commercial glucose analyzer (YSI-2700, Yellow Springs Instrument Co., OH).

A phosphate buffer YSI 2357 stabilized by 1.5 mM EDTA and 6.9 mM sodium benzoate was used (Salmon, 1991). The error caused by the addition of Ca(II)(10 mM), Cu(II)(1 mM), Mg(II)(10 mM), and Fe(III)(2.5 mM), and SL (0.4 g/L) on the analysis of glucose using the YSI glucose analyzer was determined to be 0.3, −0.8, 0.9 −2.1, and 0.6%, respectively. Therefore, the effects of metal ions and SL on the accuracy of the YSI system for glucose measurements can be ignored. All sugar measurements were performed at least twice. The averaged data were reported. The sulfonic and carboxylic group contents of the pretreated substrates were measured by a conductometric titration method (Bhardwaj et al., 2004; Katz et al., 1984).

The concentrations of soluble lignosulfonate in the washing filtrate streams were determined using a differential UV-VIS spectroscopic method (Lozovik & Kaflyuk, 2005). The absorption spectra of lignosulfonate in alkaline and neutral alcohol-water solution were recorded by a UV-VIS spectrophotometer (Model 3010, Hitachi, Japan). The absorbance at 257 nm was used for quantification. The purified lignosulfonate was used as standard for calibration. The concentrations of metal ions in substrate residuals after enzymatic hydrolysis were measured by the Analytical Chemistry and Microscopy Laboratory (USDA Forest Products Laboratory). The collected solids were air dried. Very small amounts (~1 mg) were digested in a microwave oven (MDS-2000, CEM Corp., Matthews, N.C., USA) with 5 mL of $HNO_3$ and 5 mL of 30% $H_2O_2$. ICP-AES (Ultima model, Horiba Jobin-Yvon, Edison, N.J., USA) was then used for elemental determinations.

Washing of SPORL Aspen Solid Substrate.

Washing experiments were conducted by mixing 2.0 g od SPORL substrate with different volumes (20-500 mL) of deionized (DI) water in several corresponding Erlenmeyer flasks. This is to obtain the maximal amount of removable unbound (dissolved) lignosulfonate (MARUL) from washing at several washing water temperatures, 25, 50, 65, 80, 98° C., based on dilution and extraction. DI water was first heated to a desired temperature and then poured into a flask. The flask was then set on a temperature controlled rotary incubator (Excella E25, New Brunswick Scientific Co., Edison, N.J.) at 250 rpm after adding 2.0 g od pretreated substrate. After mixing for 15 min predetermined through experiments to achieve equilibrium, about 0.6 mL sample was taken and centrifuged at 10000 g for 5 min to separate the solids from liquid. The supernatant was analyzed for lignosulfonate using UV/VIS absorption as described in Analytical Methods.

Two thoroughly washed SPORL aspen substrates were produced at temperature 25° C. and 98° C. for enzymatic hydrolysis. The washings were carried out in 5 stages using 2 g od unwashed pretreated aspen substrate and 500 mL DI water in each stage to ensure achieving maximal removal of unbound lignosulfonate, MARUL, through washing. Again the substrate was thoroughly mixed with 500 mL washing water as described above for 15 min. The substrate was then separated by filtration using Whatman No. 1 filter paper. The filter pad was collected and used for the next stage washing. The residual lignosulfonate concentration, $n_w$, in the filtrate stream of each stage was monitored using UV-Vis spectrophotometry as described in Analytical Methods and was found undetectable at the fifth stage for both washing experiments. The chemical compositions of the unwashed and two washed substrates are listed in Table 2. Washing enriched bound lignin (here refers to lignin in wood but not necessary chemically bound) and carbohydrate content by removing unbound lignin and impurities. The differences in chemical compositions between the two washed substrates at different temperatures are within the measurement uncertainties.

TABLE 2

Chemical compositions of the unwashed and washed SPORL aspen solid substrates (% w/w on oven dry basis)

| Samples | Ash | K. Lignin | Arabinan | Galactan | Glucan | Xylan | Mannan | Total Carbohydrate |
|---|---|---|---|---|---|---|---|---|
| Unwashed | 0.1 | 20.4 | 0.2 | 0.3 | 53.3 | 11.3 | 1.3 | 66.5 |
| Washed @ 25° C. | nd | 22.5 | nd | Nd | 72.7 | 2.8 | 0.3 | 75.8 |
| Washed @ 98° C. | nd | 23.6 | nd | Nd | 71.6 | 2.8 | 0.6 | 75.0 |
| Relative Standard deviations (%) | | 1.1 | 5.8 | 5.7 | 1.5 | 4.6 | 4.2 | |

Application of Additives.

Metal salts, Tween 80, and BSA were separately applied to the cellulosic substrates/buffer suspension to study the effect of these additives on enzymatic hydrolysis. Metal salts were used rather than metal alkalis, such as calcium oxide or hydroxide, to avoid the changes of pH of substrate/buffer system. Good mixing of additives with substrate suspension was achieved by setting the Erlenmeyer flask that held the suspension on the temperature controlled rotary incubator (Excella E25, New Brunswick Scientific Co., Edison, N.J.) at 200 rpm at 50° C. for 10 min. The application dosages were varied from 15-150 and 2.5-20 mg/g substrate for Tween 80 and BSA, respectively, similar to those reported in the literature (Eriksson et al., 2002; Tu et al., 2009; Yang & Wyman, 2006; Zheng et al., 2008). The dosages of metal salts, $MgSO_4$, $CaSO_4$, $CaCl_2$, and KCl ranged from 0.5-4 mmol/g substrate. The pH shift caused by these additives was minimal at less than ±0.06. A 5 g/L standard glucose solution was spiked by different additives to examine whether or not the additives affect glucose measurements. The differences in measured glucose concentrations were 0.5, 0.3, 0.9, −0.4, and −0.6% by adding K(I) at 20 mM, Mg(II) at 40 mM, Ca(II) at 25 mM, Tween 80 at 150 mg/L, and BSA at 20 mg/L, respectively. The results suggest additives did not affect glucose measurements.

Example 2

Inhibition of the Enzymatic Hydrolysis of Pure Cellulose by Unbound Lignin

Figure 4:
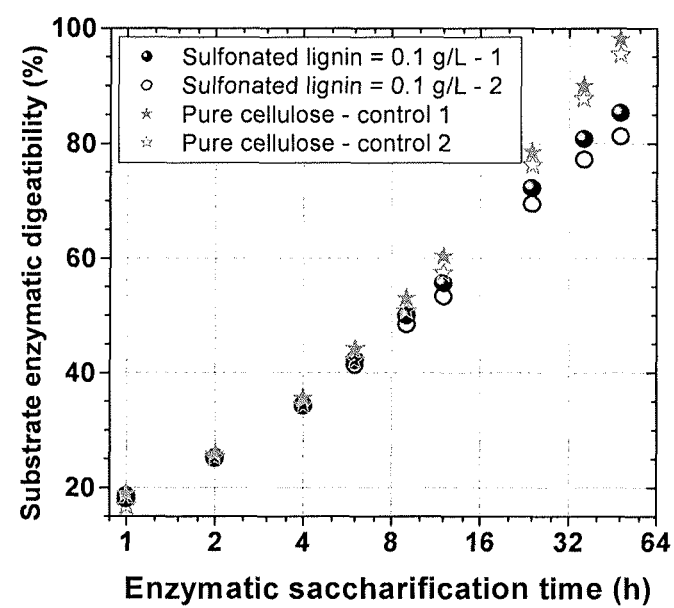
FIG. 4. Time-dependent substrate enzymatic digestibilities of pure cellulose with and without the addition of sulfonated lignin.

A few studies reported the inhibition of cellulase by unbound lignin (Sewalt et al., 1997; Berlin et al., 2005) which can be simulated by the purified lignin spiked into cellulose suspension systems. When lignin (SL) was added into pure cellulose (Whatman filter paper) suspensions at a concentration of 0.1 g/L, the substrate cellulose saccharification efficiency was decreased as reflected by the substrate cellulose digestibility (SED) (FIG. 4). SED is defined as the percentage of glucan in substrate converted to glucose by the enzymes. Time-dependent data from duplicate hydrolysis experiments of the control (no lignin addition) and with LS addition are shown in FIG. 4, which demonstrates good experimental repeatability was obtained with only a small systematic error (about 4%) at each sampling point. The duplicate experiments were conducted two weeks apart. So, the systematic errors were most likely from glucose analysis using different calibrations. The reduction in SED by SL after 48 h hydrolysis was about 14 percentage points. SED always increases as hydrolysis proceeds, and enzyme adsorption by lignin is also time-dependent. As a result, the dynamic information about the inhibition of enzymatic hydrolysis by the spiked lignin was obscured by the rapid increase in SED as hydrolysis proceeds. The data in FIG. 4 can only tell the reduction in SED at a particular time.

Figure 5:
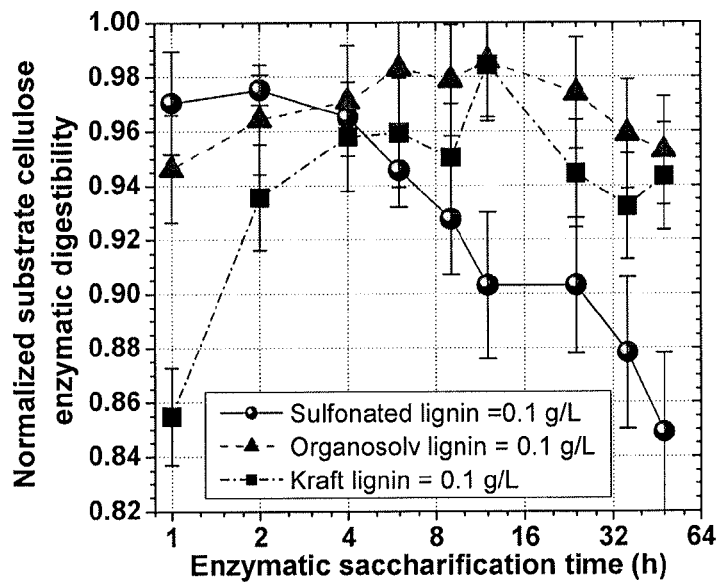
FIG. 5. Effects of different types of lignin at 0.1 g/L on normalized time-dependent enzymatic digestibility of pure cellulose.

To illustrate the dynamic behavior of nonproductive adsorption of enzymes by lignin, each SED data point from a lignin-spiked experiment was normalized by the corresponding SED at the same hydrolysis time of the pure cellulose (control) experiment. The normalized SED after 48 h hydrolysis was decreased by 15% when SL was added (FIG. 5). When the same amount of OL or KL was added, the SED was reduced by about 6% (FIG. 5). This could be due to the differences in the affinity of different lignin with enzymes. The hydrophilic nature of SL may result in a stronger affinity to enzymes. The lignin solubility may also play a role. SL is soluble at pH of 4.8 whereas OL and KL are not. The reduced SED is a result of nonproductive enzyme adsorption onto lignin as reported in the literature (Eriksson et al., 2002; Mansfield et al., 1999; Yang and Wyman, 2006; Zheng et al., 2008; Sewalt et al., 1997).

The time-dependent SED data suggest there are competing physical and chemical processes taking place in the lignin-containing aqueous cellulose-enzyme suspensions. Because of the soluble nature of SL, SED decreased with hydrolysis time continuously when SL was added (FIG. 5). As described in the Materials and Methods Section, the KL or OL solution (pH=12) was added and pre-incubated on the shaking bed for 15 min first before enzymes were added to beginning hydrolysis. However, KL and OL are not soluble in the aqueous cellulose-enzyme suspension of pH about 4.8. KL and OL precipitation occurred. The precipitation process of the dissolved KL and OL in the alkaline solution onto the cellulose substrate is similar to that which occurred during washing of Organosolv and Kraft pulps. Washed Kraft and Organosolv fiber surfaces were covered by an adsorbed layer of reprecipitated lignin (Xu et al., 2007; Simola et al., 2000). This suggests that a similar layer of reprecipitated lignin covered the cellulose surface after KL or OL lignin solution was added, which resulted in a significant reduction (15 percentage points) in SED at the beginning of the hydrolysis (FIG. 5). As hydrolysis proceeds, the cellulose fibers were broken down by the enzymes, which increased the cellulose accessibility to the enzymes and effectively reduced the cellulose covering area by KL. As a result, SED mostly recovered by 4 h (FIG. 5). The desorbed lignin can still bind with enzymes, which continues to suppress enzyme activities and therefore SED (FIG. 5). Similar explanations can be applied to the data set for OL.

The results (FIG. 5) have significant implications to all pretreatment technologies that remove a fraction of biomass lignin, especially to the two most robust biomass pretreatment processes for sugar and ethanol production, Organosolv (Pan et al., 2006) and SPORL (Zhu et al., 2010a; Zhu et al., 2010b). Organosolv pretreatment dissolves as much as 70% of biomass lignin (Pan et al., 2006) into the pretreatment hydrolysate. SPORL can remove about 20-40% of biomass lignin (Zhu et al., 2009; Wang et al., 2009) in the form of lignosulfonate. The results from the KL addition experiment suggest that certain alkaline pretreatments will suffer from the same consequence of nonproductive enzyme adsorption by unbound lignin. A thorough washing of lignocellulose solid substrate has been applied as a common practice to reduce nonproductive adsorption before enzymatic hydrolysis.

Figure 6:
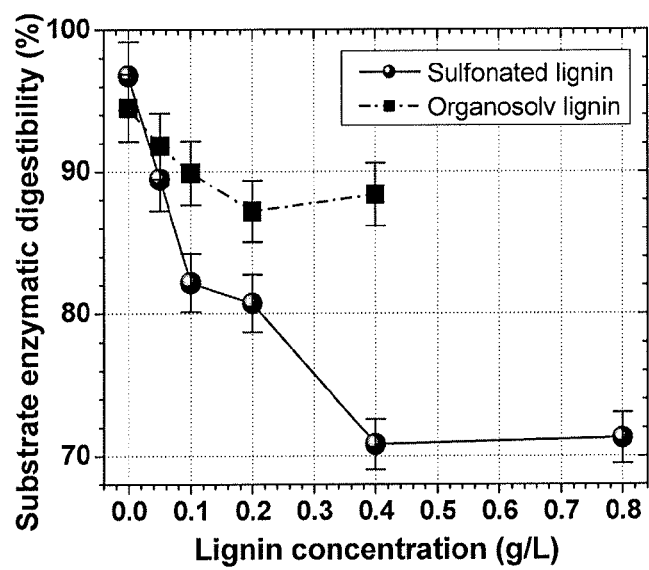
FIG. 6. Effects of the amount of sulfonated and Kraft lignin added on enzymatic digestibility of pure cellulose measured at 48 h.

To further evaluate the effect of unbound lignin on enzymatic hydrolysis of solid lignocellulosic substrate, different amounts of OL and SL were added to the pure cellulose substrate suspension before enzymatic hydrolysis. The increases in lignin (OL or SL) concentration in the aqueous substrate suspension resulted in further inhibition of cellulose saccharification as observed from the reduced normalized SED after 48 h hydrolysis (FIG. 6). Fortunately, the reduction in SED reached an asymptotic value at OL and SL concentrations of 0.2 and 0.4 g/L, respectively. These two critical lignin concentrations may be related to the amount of enzyme applied and the solubility of lignin (OL only) in the aqueous hydrolysis system of pH around 4.8.

Example 3

Figure 7:
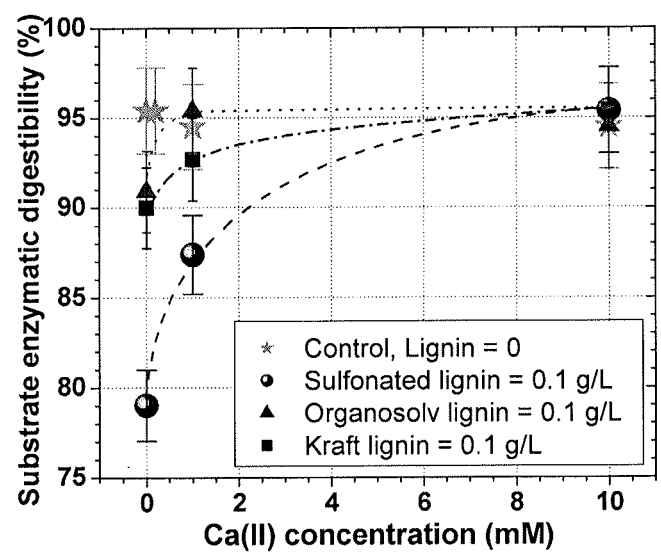
FIG. 7. Recoveries of pure cellulose enzymatic digestibility measured at 48 h by the addition of $CaCl_2$ in a cellulose-enzyme system containing different types of lignin at 0.1 g/L.

Calcium(II) to Reduce Inhibition of Enzymatic Cellulose Hydrolysis by Unbound Lignin It is hypothesized that lignin-metal complexes can reduce nonproductive enzyme adsorption in aqueous cellulose-enzyme systems. Different amounts of $CaCl_2$ were added into the pure cellulose suspensions that contained 0.1 g/L lignin (OL, KL, or SL) before enzymatic hydrolysis. It was found that $CaCl_2$ has no effect on enzymatic hydrolysis of pure cellulose without the addition of lignin (FIG. 7). The slight reduction of about 1% in saccharification efficiency at Ca(II) concentration of 10 mM is within the measurement uncertainty. When $CaCl_2$ was added into lignin containing cellulose suspensions, the recoveries of SEDs are obvious (FIG. 7). With the addition of Ca(II) to a concentration of just 1 mM, 50% or more of the reduction in cellulose saccharification caused by lignin addition was recovered for all the lignin-containing cellulose suspensions. The reduction in SED due to lignin addition was almost completely eliminated at Ca(II) concentration of 10 mM.

Figure 8:
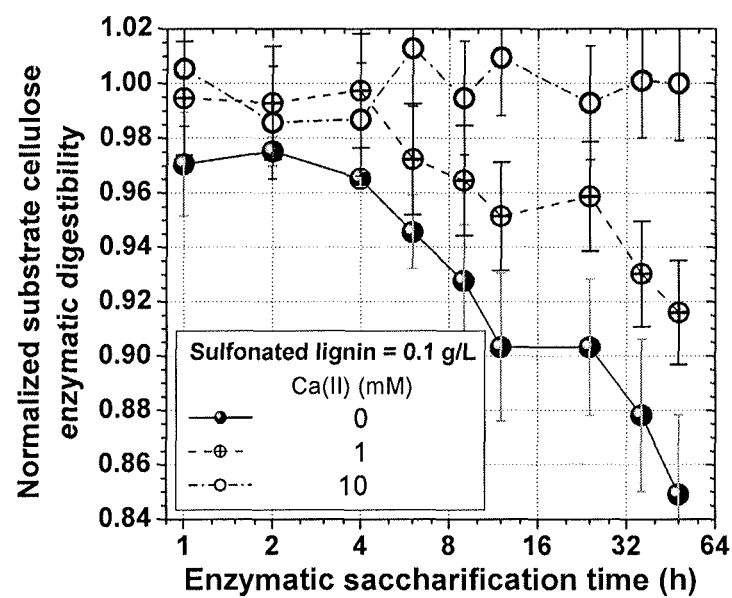
FIG. 8. Recoveries of the time-dependent enzymatic digestibility of pure cellulose by the addition of $CaCl_2$ in a cellulose-enzyme system containing sulfonated lignin at 0.1 g/L.

The effectiveness of Ca(II) for reducing non-productive enzyme adsorption can also be observed from the time-dependent enzymatic saccharification efficiency of pure cellulose with the addition of lignin (FIG. 8). When SL was added into the pure cellulose suspension to a concentration of 0.1 g/L, the normalized SED by the corresponding SED of the pure cellulose system at the same hydrolysis time was reduced by 3% after the first hour of hydrolysis and further decreased by 15% after 48 h. When $CaCl_2$ was added into the suspension to a Ca(II) concentration of 1 mM, the reduction in SED by SL at 48 h recovered by 50% (FIG. 8). When Ca(II) concentration was increased to 10 mM, the inhibition of enzymatic hydrolysis by the added SL was almost completely eliminated throughout the entire hydrolysis process. It was reported that calcium ion can bind to lignisulfonate-sodium plasticizer (Grierson et al., 2005) and calcium ion can also exchange sodium ion on SL in neutral solutions in room temperature (Zakis, 1994). These suggest that the sodium based SL used in this Example serves as a chelating agent to bind calcium ions to form complex. This complex has low affinity to cellulase enzymes which reduced nonproductive enzyme absorption and resulted in the observed enhancement in enzymatic hydrolysis of cellulose.

Example 4

Figure 9:
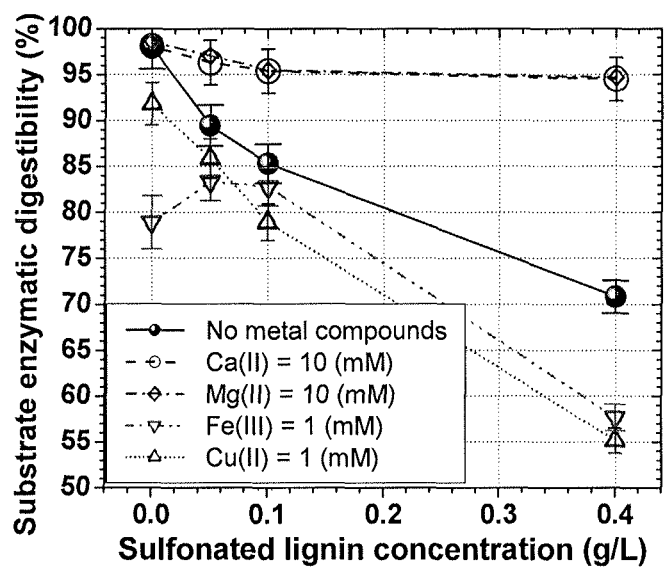
FIG. 9. Effects of the additions of different metal compounds on enzymatic digestibility of pure cellulose measured at 48 h in a cellulose-enzyme system containing sulfonated lignin at 0.1 g/L.

Effect of Other Metals on Enzymatic Cellulose Hydrolysis in the Presence of Unbound SL The effectiveness of various metal compounds for reducing lignin inhibition of enzymatic cellulose hydrolysis was evaluated. Pure cellulose suspensions in the presence of SL with a concentration range up to 0.4 g/L were added with different metal compounds before hydrolysis. Cu(II) was known to be toxic to most cellulase enzymes. The addition of $CuCl_2$ to a Cu(II) concentration of just 1 mM produced additional significant reduction in SED of the substrate cellulose (FIG. 9). The addition of $FeCl_3$ showed the similar results to those obtained using $CuCl_2$. The addition of $CaCl_2$ to a Ca(II) concentration of 10 mM effectively eliminated the inhibition of enzymatic hydrolysis by SL in the concentration range tested up to 0.4 g/L (FIG. 9). The results clearly show that the addition of $MgSO_4$ to a Mg(II) concentration of 10 mM also effectively eliminated inhibition of enzymatic hydrolysis by SL. It is known that Ca(II) is nontoxic to yeast and Mg(II) has a positive effect on yeast growth in fermentation within certain concentration ranges, therefore, the addition of Ca(II) or Mg(II) may improve simultaneous enzymatic saccharification and fermentation using unwashed or less washed solid substrate to reduce water consumption in production.

Example 5

Figure 10:
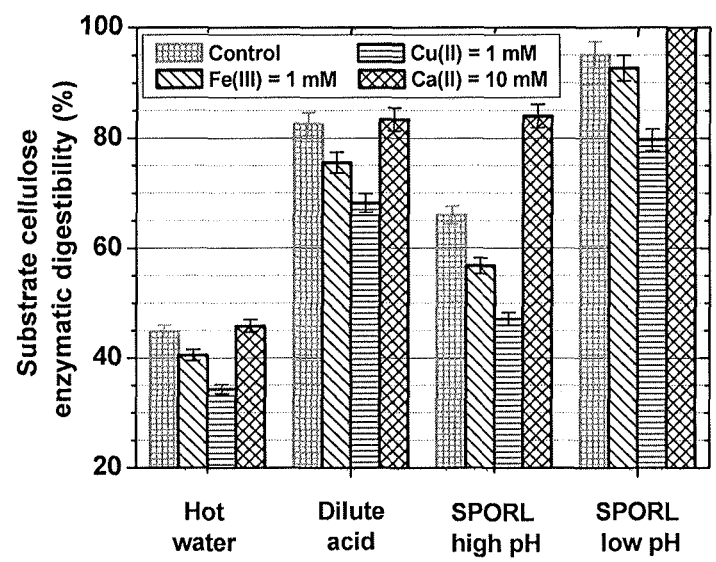
FIG. 10. Effects of the additions of different metal compounds on enzymatic digestibilities of washed pretreated-eucalyptus substrates measured at 48 h.

Ca(II) to Reduce Inhibition of Enzymatic Cellulose Hydrolysis by Lignin in Pretreated Wood Substrate Reducing the inhibition of cellulase activities by lignin in lignocellulosic substrate can improve biomass substrate saccharification efficiency. $CaCl_2$, $CuCl_2$, and $FeCl_3$ were separately applied to enzymatic hydrolysis of each of four eucalyptus substrates produced by hot-water, dilute-acid, and SPORL high pH, and SPORL low pH pretreatment. Different pretreatments resulted in very different substrate enzymatic cellulose digestibility (FIG. 10). The addition of $CuCl_2$ and $FeCl_3$ reduced SED as expected based on the discussions in Example 4. The addition of $CaCl_2$ with Ca(II) concentration of 10 mM in the substrate suspension increased SED for two SPORL pretreated substrates tested (FIG. 10). The increase was especially significant for the SPORL high pH substrate with an increase in SED of about 20 percentage points (or about 27%). Complete enzymatic cellulose saccharification of the SPORL low pH substrate was achieved. However, the increase was not obvious for the hot-water and dilute-acid pretreated substrates. The difference in the effectiveness of $CaCl_2$ addition on enhancement of cellulose enzymatic saccharification efficiency of different substrates may be explained by the difference in lignin chemical structure or functional groups that can interact with metal ions to form lignin-metal complex. A high degree of sulfonation may promote the formation of lignin-metal complex. The higher sulfonic acid group content of SPORL high pH substrate than that of the SPORL low pH substrate (Table 1) may explain the difference in the enhancement of SED of these two substrates when the same amount of 10 mM Ca(II) was applied. On the other hand, no sulfonation reaction occurred during the dilute-acid and hot-water pretreatment as evidenced by the measured sulfonic acid group content (Table 1). Moreover, washing removed almost all of the unbound lignin on the pretreated wood substrates. As a result, no obvious effective enhancement of SED of the dilute-acid pretreated substrates (hot-water is a special case of dilute-acid pretreatment) was observed (FIG. 10).

Figure 11:
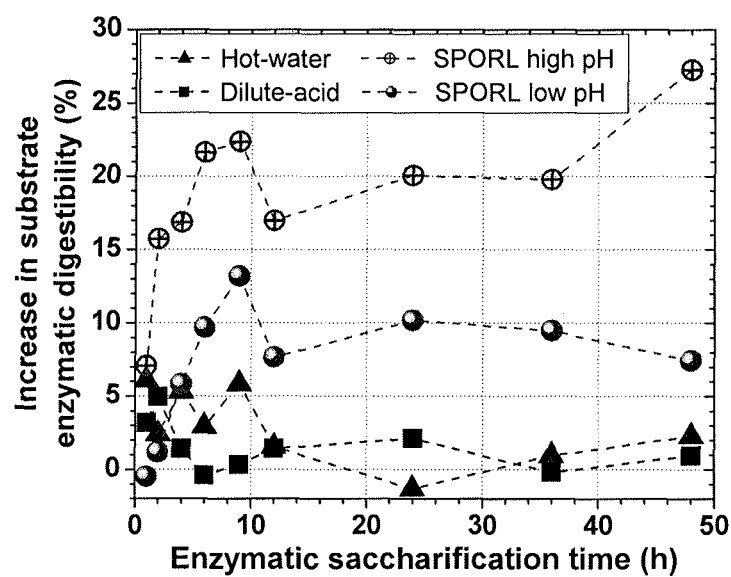
FIG. 11. Time dependent enhancement of cellulose saccharification efficiency of the 4 substrates by the addition of $CaCl_2$ at Ca(II) concentration of 10 mM.

The time dependent enhancement of cellulose saccharification efficiency of the four substrates by the addition of $CaCl_2$ at Ca(II) concentration of 10 mM was presented in FIG. 11. The results show that the effectiveness of Ca(II) addition is not visible for the two dilute-acid pretreated substrates. The results also show the graduate increase in the enzymatic cellulose saccharification efficiency of the two SPORL substrates in the first 6 hours of hydrolysis. The cellulose saccharification efficiencies level out thereafter. This temporal characteristic represents the dynamic and competing processes of the formation of lignin-metal complex and the adsorption of enzymes onto lignin.

Both the bound lignin on solid substrate and the unbound lignin (can be dissolved or insoluble) in the lignocellulosic substrate-enzyme system can inhibit cellulose enzymatic hydrolysis through non-productive adsorption of enzymes. The application of Ca(II) and Mg(II) were proven to be effective at reducing or eliminating both unbound and bound lignin inhibition likely through the formation of lignin-metal complex. A plausible explanation for this is that the lignin-metal complexation can deactivate the enzyme adsorption sites. This mechanism can be validated by enzyme adsorption measurement in future studies. The time-dependent SED data presented in this Example represent the dynamic and competing processes of the formation of lignin-metal complex and the adsorption/desorption of enzymes.

Example 6

Figure 12:
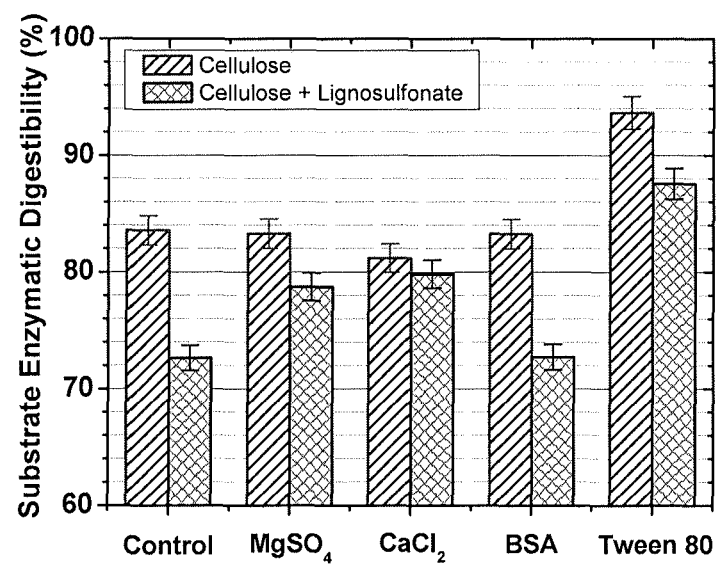
FIG. 12. The effects of the application of purified lignosulfonate and different additives on enzymatic digestibility of pure cellulose. Cellulase loading=10 FPU/g cellulose.

Effect of Unbound Lignosulfonate on Cellulase Hydrolysis of Pure Cellulose and the Abilities of Metal Salts, BSA, and Tween 80 to Reverse this Effect The inhibition of enzymatic cellulose hydrolysis by unbound lignosulfonate was further evaluated by spiking purified lignosulfonates into a pure cellulose suspension. Commercial lignosulfonate was found to inhibit enzymatic hydrolysis of pure cellulose as discussed in Example 2. It has been demonstrated that Ca(II) can eliminate this inhibition through the formation of lignin-Ca(II) complex. By using purified lignosulfonate derived from SPORL, the potential of various metal salts for enhancing enzymatic hydrolysis of unwashed lignocelluloses from SPORL can be demonstrated. The pure cellulosic substrate enzymatic digestibility (SED), determined as the percentage of glucan enzymatically hydrolyzed to glucose in 48 hours at a 1% w/w substrate solid loading, decreased from 84 to 73% in the presence of 50 mg of purified lignosulfonate per g cellulose (or 5% w/w) (FIG. 12). This is in agreement with prior research using milled wood lignin or hydroxypropylated lignin (Sewalt et al., 1997). In quantitative terms, this corresponds to reduce of 0.22% g cellulose/mg purified lignosulfonate at a cellulase loading of 10 FPU/g cellulose. This value is named the unbound lignin inhibition potential (LIP). LIP can be defined as follows, $$LIP = \lim_{\substack{lignin=0 \\ enzyme \to o}} \frac{d(SED)}{d(Lignin)} \quad (1)$$

The value of 0.22% g cellulose/mg lignin is an average value and is much smaller than those obtained previously using a commercial lignosulfonate in Example 2. The LIP values obtained previously were >1% g cellulose/mg lignin at lignosulfonate dosage less than 40 mg/g cellulose and a lower enzyme loading of 7.5 FPU/g cellulose. The differences in lignin itself may be a factor as well as the lower lignin dosages and enzyme loading.

Metal salts $CaCl_2$ and $MgSO_4$ were separately added to pure cellulose suspensions spiked with purified lignosulfonate to verify the previous results. It has been demonstrated the complete elimination of the inhibition of enzymatic hydrolysis by lignin including lignosulfonate (0.1 g/L or 5 mg/g cellulose) spiked into a pure cellulose suspension by the application of metal salts, $CaCl_2$ and $MgSO_4$, at a concentration of 10 mM, or 1 mmol/g cellulose. The purified lignosulfonate dosage was increased to 50 mg/g cellulose in this Example. It should be pointed out that it has been found previously that the cellulose inhibition by the spiked lignin reached an asymptotic value using a dosage of about 20 mg/g cellulose with a commercial lignosulfonate. The present results indicate that the applications of $CaCl_2$ or $MgSO_4$, have no effect on enzymatic hydrolysis of pure cellulose (without lignosulfonate). The measured substrate enzymatic digestibilities (SEDs) were all about 83%, the same as the pure cellulose, or control run without the added metal salts (FIG. 12). When $CaCl_2$ and $MgSO_4$ were separately applied to the cellulose suspension spiked with 50 mg/g cellulose purified lignosulfonate, SED was increased from 73% to about 80%. Quantitatively, the application of $CaCl_2$ and $MgSO_4$ at a dosage of 1 mmol/g cellulose eliminated about 65% of the inhibition of enzymatic cellulose hydrolysis by the spiked lignosulfonate.

Tween 80 and BSA were also separately applied to the same pure cellulose suspension treated at the same enzyme dosage of 10 FPU/g cellulose, for comparison. It was found that applying BSA at 10 mg/g cellulose was ineffective, demonstrating it had no effect on unbound lignosulfonate (spiked). The application of Tween 80 at 15 mg/g cellulose improved SED from 83 to 94% and 73 to 88% (FIG. 12), respectively, for the pure cellulose and lignosulfonate spiked cellulose suspensions. It is known that surfactants can improve enzymatic hydrolysis of pure cellulose and lignocellulose (Eriksson et al., 2002; Helle et al., 1993; Mizutani et al., 2002; Sewalt et al., 1997). These earlier studies suggested that surfactant enhances cellulose hydrolysis through reducing nonproductive attachment/adsorption of endoglucanase to cellulose and lignin, and also by disrupting cellulose structure and increasing enzyme accessibility to cellulose. In comparison, metal salts are only expected to reduce non-productive adsorption of enzymes by complexing with the lignin. As a result, Tween 80 is more effective in enhancing SED for the two cellulosic suspensions studied.

Example 7

Determination of the Maximal Amount of Removable Unbound Lignosulfonate by Washing at Different Temperatures The washing of SPORL lignocellulosic substrate to remove unbound lignin follows a dilution and extraction mechanism (Crotogino et al., 1987). The maximal amount of removable unbound lignosulfonate (MARUL) from the initial unwashed substrate, $m_0$, can be determined by measuring the unbound lignosulfonate concentration in the diluted substrate suspension after adding washing water, $n_w$, based on mass balance as follows, $$m_0 = n_w(V_0 + V_w) \quad (2)$$

where V0 is the unknown volume of the water (moisture) in the initial unwashed wet substrate and Vw is the volume of dilution water used in washing. Equation (2) can be rewritten as, $$\frac{1}{n_w} = \frac{V_0}{m_0} + \frac{V_w}{m_0} \quad (3)$$

Figure 13A:
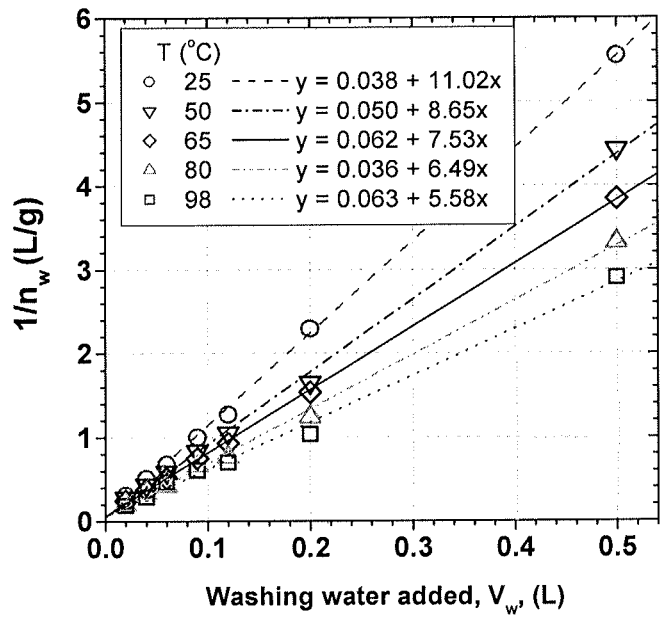
FIGS. 13A-13B.

The MARUL through washing, $m_0$, can be determined through linear regression of the measured $n_w$ and $V_w$, i.e., $m_0$ is the inverse of the slope of Eq. (3). $n_w$ and $V_w$ can be obtained by conducting a set of washing experiments using different amounts of washing water (dilutions) at a given washing temperature or pressure. The results showed excellent linear relationships between $1/n_w$ and $V_w$ for the 5 sets of washing experiment conducted at 5 different temperatures (FIG. 13A).

Figure 13B:
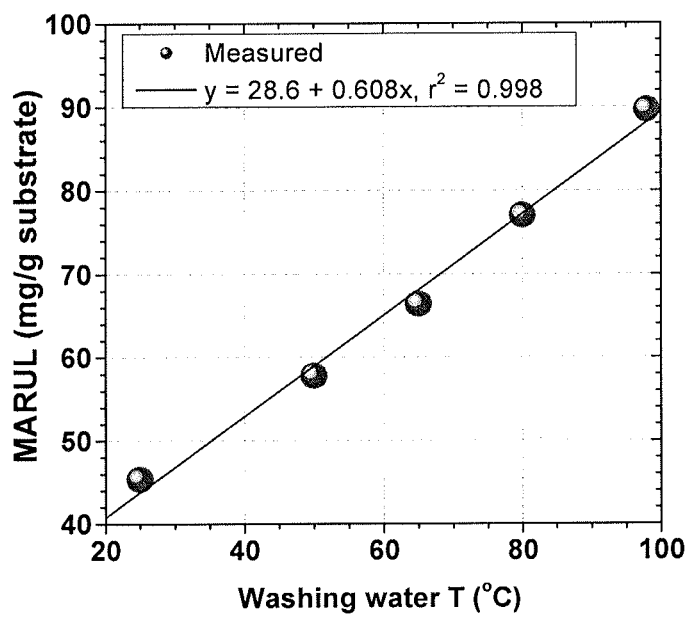

It is known that washing efficiency can be improved by heating wash water and by increasing the solubility of impurities. The results indicate that MARUL, $m_0$, determined from the data in FIG. 13A was linearly proportional to washing water temperature (FIG. 13B) in the temperature range studied. At 25° C., $m_0$ was about 45.4 mg from washing 1 od g substrate (85.1 mg/g cellulose based on glucan content of unwashed substrate). When washing water temperature was increased to 98° C., $m_0$ was almost doubled to 89.6 mg/g od substrate (or 168.1 mg/g cellulose), or about 9% of the lignocellulosic substrate solids. Because both lignin sulfonation and condensation reactions could occur during SPORL (acid sulfite pretreatment), a high washing water temperature increased the solubility of the re-precipitated lignin (Adler, 1977; Nagle et al., 2002).

Example 8

Figure 14:
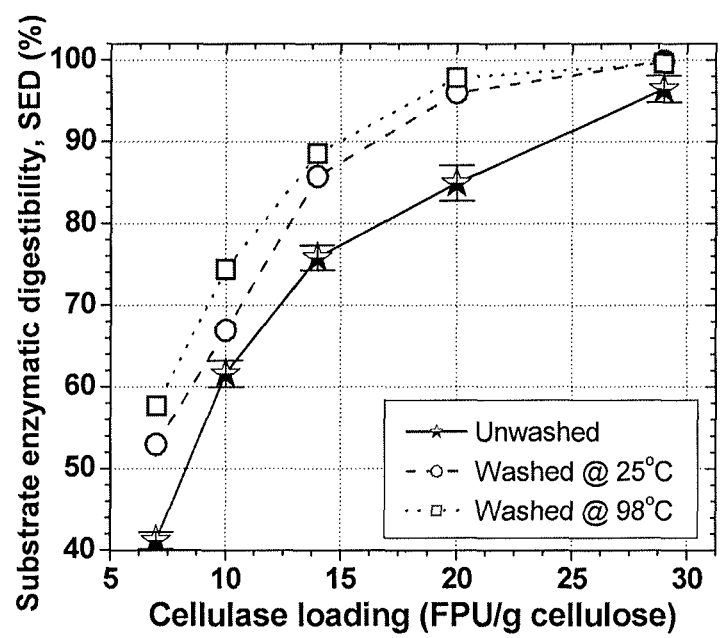
FIG. 14. The effects of washing on substrate enzymatic digestibility (SED) of a SPORL aspen substrate at various enzyme loadings. Averages were plotted for all curves.

Quantification of Enzymatic Hydrolysis Inhibition by Soluble Components in an Unwashed SPORL Aspen Substrate Substrate enzymatic digestibilities (SEDs) of unwashed and washed SPORL aspen substrates were compared to verify the inhibitory effect of soluble components in the pretreatment hydrolysate, including that of unbound lignosulfonate. The comparative experiments were conducted at several enzyme loadings using the unwashed and two thoroughly washed substrates at 25 and 98° C., respectively. The results clearly show that washing improved SED at 48 h for all the enzyme loadings studied (FIG. 14). Washing at 98° C. removed more unbound lignosulfonate than at 25° C. (FIG. 13B) and, further, improved SED for all the enzyme loadings studied (FIG. 14). The improvements are most significant at low enzyme loadings and diminished at very high enzyme loadings. For example, SED was improved by 30 and 40%, respectively, by washing at 25 and 98° C. at enzyme loading of 7 FPU/g cellulose. The SED improvements were less than 5% at enzyme loading of 29 FPU/g cellulose. The observed effects of washing on SED improvement agree with those reported in the literature (Sinitsyn et al., 1982; Tengborg et al., 2001). The amount of lignosulfonate removed can be used as surrogate of the total soluble inhibitors to estimate this inhibitory effect. The total amount of unbound lignosulfoante removed is assumed to be equal to the MARUL, 168.1 and 85.1 mg/g cellulose, obtained from washing at 98 and 25° C., respectively. The results (Table 3) clearly shows the marginal inhibitory effect decreases with the increase in (1) enzyme loading due to the availability of more free cellulase, and (2) lignosulfonate content of the substrate. The estimated degrees of enzymatic hydrolysis inhibition (Table 3) of the 25° C. washed substrate are about the same as the 0.22% g cellulose/mg lignosulfonate quantified using pure cellulose spiked with purified lignosulfonate, except at very high enzyme dosages of 20 FPU/g cellulose and greater. It should be pointed out that the adsorbed soluble glucose on the substrate (washed at 50° C.) is less than 9 mg/g unwashed substrate, not considerable enough to cause end product inhibition (Holtzapple et al., 1990).

Example 9

Eliminating Inhibition of Enzymatic Hydrolysis by Lignosulfonate in an Unwashed SPORL Aspen Substrate Using Metal salts, BSA, and Tween 80

Figure 15:
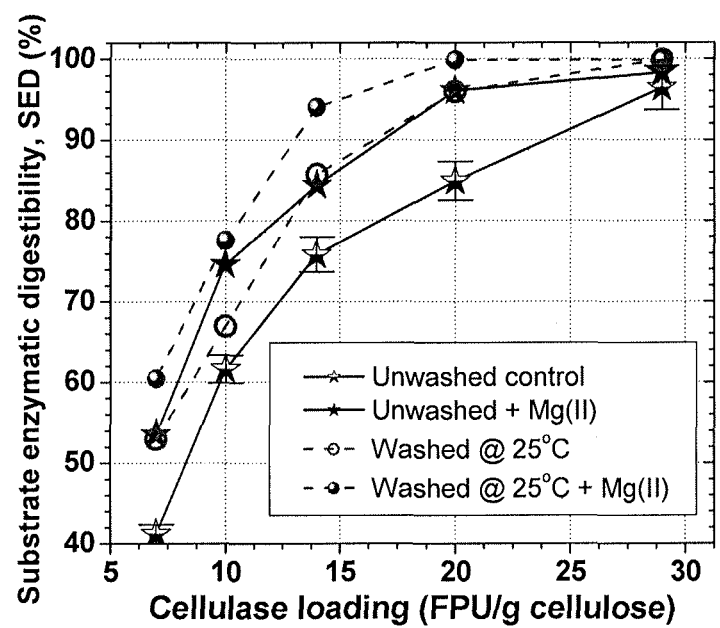
FIG. 15. The effects of $MgSO_4$ application (1 mmol/g substrate) on SED of unwashed and washed at 25° C. aspen substrate at various enzyme loadings.
Figure 16:
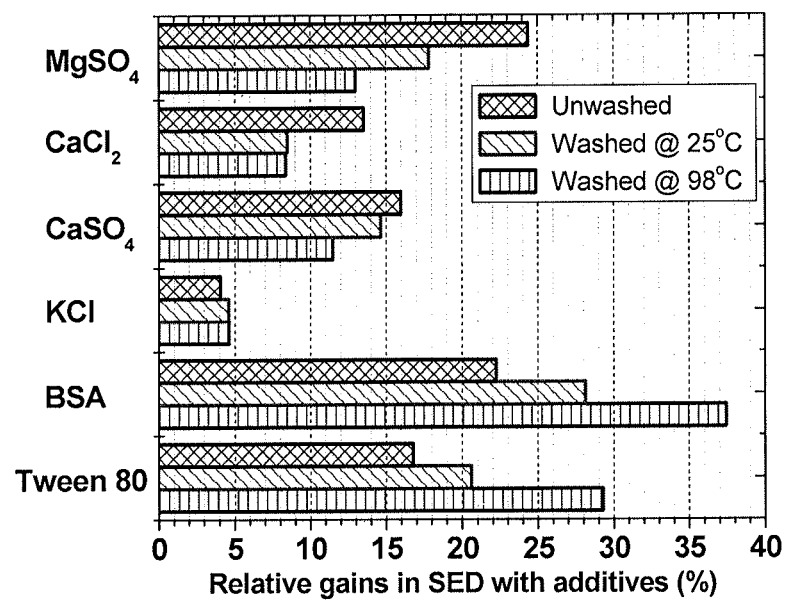
FIG. 16. Relative (to control) gains in SED by the application of various additives for the unwashed and two washed SPORL aspen substrates. Additive dosages: Ca(II) and Mg(II)=1 mmol/g substrate; K(I)=2 mmol/g substrate; Tween 80=15 mg/g substrate; BSA=10 mg/g substrate. Control=no additive. Cellulase loading=5 FPU/g substrate.

Metal salts along with BSA and Tween 80 were separately applied to enzymatic hydrolysis of the unwashed and two thoroughly washed SPORL aspen substrates to evaluate the potentials of these additives for eliminating substrate washing. When 1 mmol $MgSO_4$/g substrate was applied, the SEDs of the unwashed substrate matched the corresponding SED of the washed substrate without $MgSO_4$ in a wide range of enzyme loadings (FIG. 15). $MgSO_4$ was effective on both unwashed and washed substrate in improving SED (FIGS. 15-16). This clearly suggests that washing at 25° C. can be completely eliminated with the application of $MgSO_4$ at 1 mmol/g substrate without sacrificing SED. Moreover, the SED of the substrate washed at 25° C. with the application of $MgSO_4$ are higher than its corresponding value of the substrate washed at 98° C. at the same enzyme loading for the range of enzyme loadings studied. Therefore, $MgSO_4$ can substitute for hot washing when further improvement of SED is desired.

Similar effects were observed using other metal salts at 1 mmol/g substrate with an enzyme loading of 5 FPU/g substrate (FIG. 16). All tested metal salts improved SED of the two washed substrates with smaller relative gains in SED than that of the unwashed substrate (FIG. 16). This is, firstly, because bound lignin contains acidic groups (Liu et al., 2010), although at a much lower fraction than unbound lignosulfonate, which serve as binding sites for metal ions (Torre et al., 1992), to form lignin-metal complexes. Secondly, some bound lignin was released into the substrate suspension from the lignocellulosic substrates, becoming unbound, due to the release of glucan by enzyme actions as hydrolysis proceeds. This unbound lignin may also have binding sites for cellulase. Because the washed substrates have significantly lower amounts of unbound lignosulfonate, especially the substrate washed at 98° C., than the unwashed substrate, the relative gains in SED of the washed substrates are lower than that of the unwashed substrate with the application of metals. The relative gain in SED of the substrate washed at 98° C. is the smallest among the three substrates studied. The slight improvement of about 4% in SED with the application of KCl (2 mmol/g substrate) on the three substrates is probably simply due to the increase in ionic strength. It was suggested that

TABLE 3

Effects of washing and increase cellulase loadings on lignin inhibition of enzymatic hydrolysis of the SPORL aspen substrate

| Enzyme loadings (FPU/g cellulose) | SED of unwashed substrate (%) | SED Gains with washing @ 25° C. | SED Gains with washing @ 98° C. | SED reduction of substrate washed at 25° C. (% g cellulose/mg lignin) [a] | SED reduction of unwashed substrate (% g cellulose/mg lignin) [b] |
|---|---|---|---|---|---|
| 7 | 41.2 | 19.2 | 21.2 | 0.226 | 0.126 |
| 10 | 61.6 | 16.0 | 17.5 | 0.188 | 0.104 |
| 14 | 75.8 | 18.2 | 19.6 | 0.214 | 0.117 |
| 20 | 85.0 | 14.9 | 14.6 | 0.175 | 0.087 |
| 29 | 96.4 | 3.4 | 3.4 | 0.040 | 0.020 |

[a] amount of unbound lignosulfonate removed: 85.1 mg/g cellulose
[b] amount of unbound lignosulfonate removed: 168.1 mg/g cellulose high ionic strength can promote enzymatic hydrolysis of cellulose (Reinikainen et al., 1995).

The application of BSA (10 mg/g substrate) and Tween 80 (15 mg/g substrate) are more effective on the two washed substrates which have relatively lower unbound and higher bound lignin content than the unwashed substrate (FIG. 16), opposite to what was observed when metal salts were applied. This is because BSA cannot overcome inhibition of enzymatic hydrolysis by unbound lignosulfonate based on the study using pure cellulose (FIG. 12). Its effect on enhancing enzymatic hydrolysis is through reducing inhibition by blocking non-productive adsorption of enzyme only onto bound lignin. It should be pointed out that the applied dosages of BSA and Tween 80 are high from economical point of view when comparing with calcium salts.

Figure 17:
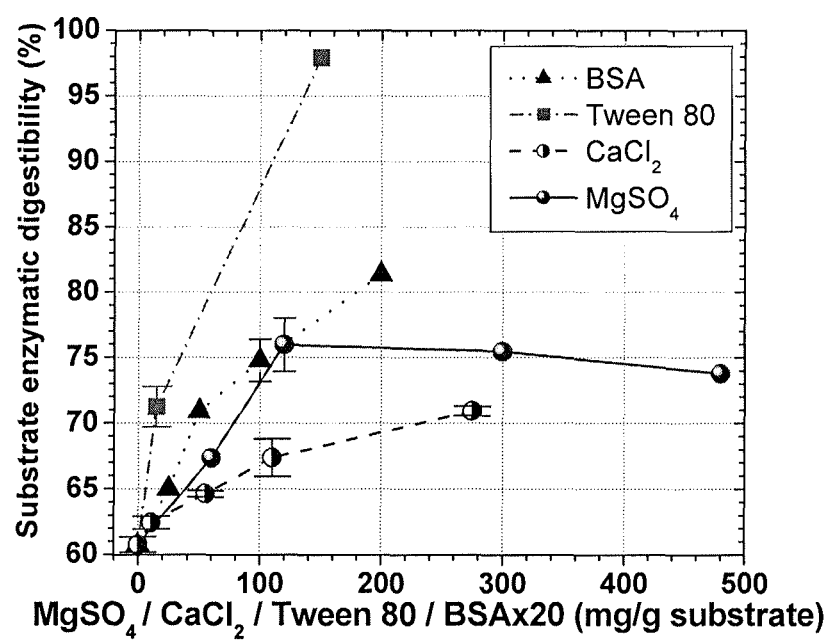
FIG. 17. The effects of additive dosages on SED of the unwashed SPORL aspen substrate. Cellulase loading=5 FPU/g substrate.

The effects of the application dosages of additives on improving SED of unwashed substrate were also studied at an enzyme loading of 5 FPU/g substrate (or 9.4 FPU/g cellulose). SED increases with the increase in $CaCl_2$ and $MgSO_4$ dosage from 60% and then reached an asymptotic value of about 75% (FIG. 17). The 15 percentage point gain in SED corresponds to the total inhibition by the unbound lignosulfonate in the unwashed substrate. This can be seen from the difference of SEDs between the unwashed and washed at 98° C. substrates at the same enzyme loadings (FIG. 14). This suggests that the application of 1 mmol/g substrate $MgSO_4$ completely eliminated the inhibition of enzymatic hydrolysis by unbound lignosulfonate in unwashed substrate. As a result, further improvement in SED is not possible at higher $MgSO_4$ dosages (FIG. 17). The increase in the dosage of BSA and Tween 80 also enhanced SED of unwashed substrate (FIG. 17). The slope of the BSA curve is about the same as that of the $MgSO_4$ curve (FIG. 17). Although the Tween 80 curve has a much steeper slope, the Tween 80 dosage of 15 mg/g substrate is regarded as high in practical applications.

Figure 18:
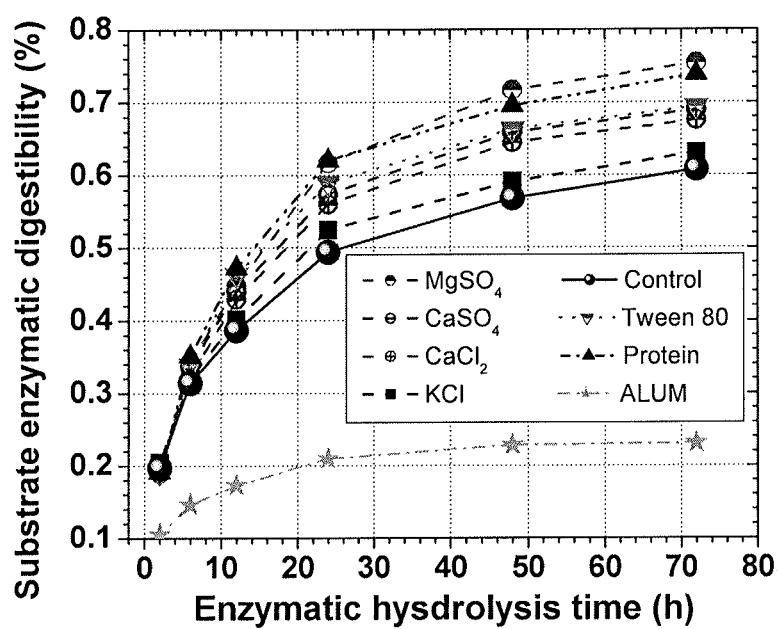
FIG. 18. Effect of different metal compounds and additives on time-dependent Unwashed substrate enzymatic digestibility. Additive dosage on g substrate: All metals: 10 mM ($MgSO_4$: 12 mg/g); Tween 80: 15 mg/g; bovine serum albumin-BSA (Protein): 10 mg/g.

Effect of different metal compounds and additives on time-dependent unwashed substrate enzymatic digestibility was also studied (FIG. 18). Aspen substrate was pretreated by SPORL at 170° C., with sodium bisulfate charge of 3% and acid charge 1% both on oven dry wood base for 25 min in a batch reactor. Substrate was produced by milling the pretreated wood chips using a disk refiner with very low energy consumption of 30 kWh/ton wood.

Figure 19:
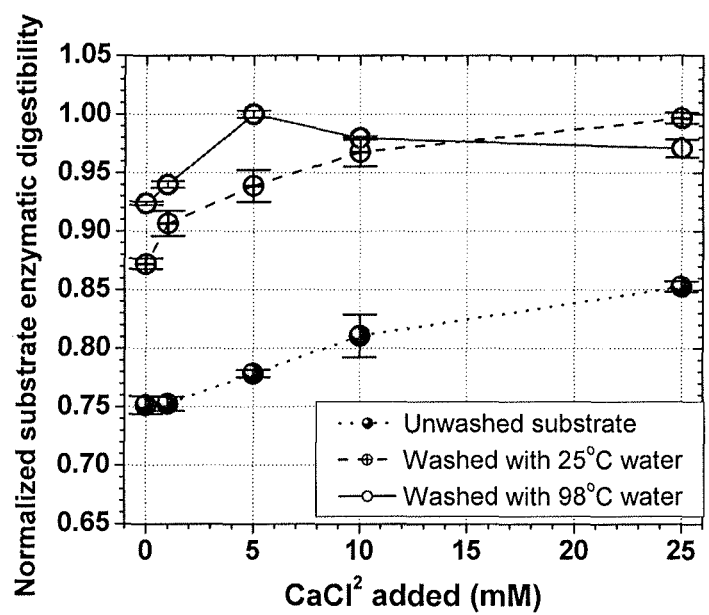
FIG. 19. Effect of $CaCl_2$ addition on enhancing enzymatic digestibility of unwashed, washed (low T) and washed (high T) substrates.

Effect of $CaCl_2$ ($CaSO_4$ and $MgSO_4$ were also tried and had better effect; $CaCO_3$ will be tried) addition on enhancing enzymatic digestibility of unwashed, washed (low T) and washed (high T) substrates (FIG. 19). The results were obtained using the Aspen substrate described in [00145] The enzymatic hydrolysis experiments were conducted using unwashed substrate, washed with 25° C. water, and washed with 98° C. water (to simulate high P, high T washing). Very low dosage of enzyme of only 5 FPU/g substrate was used in enzymatic hydrolysis. The data presented were after 48 h hydrolysis normalized by the highest cellulose conversion rate achieved of all the experiments conducted. The results indicate that wash with 25° C. is more than enough to achieve maximal substrate cellulose conversion with $CaCl_2$ addition even at very low enzyme dosage. Even without washing at all, an enzymatic digestibility of 85% maximal can be achieved with 25 mM $CaCl_2$ addition. It can be concluded that only minimal washed is required with process water (typically about 50° C.).

The application of metal salts may not only affect the fermentability of the resultant hydrolysate, but also impact lignin recovery due to the formation of lignin-metal complex. The metal ions retained on the residual solid substrate at the completion of enzymatic hydrolysis were analyzed. The hydrolysis residual solids yields were estimated by subtracting the measured glucan loss through hydrolysis from the initial substrate mass. The metal ion contents on the residual solids were only about 1-2% of the dosage applied (Table 4). Hydrolysis was conducted at 1% solids consistency with the addition of metal salts at a dosage of 2 mmol/g substrate for KCl and 1 mmol/g substrate for all other metal salts. Solids yield after enzymatic hydrolysis is estimated by subtracting the measured glucan loss (by hydrolysis) from the initial solids. This suggests that the application of metal compounds should not have significant effects on the utilization of lignin from the solid residual. If $MgSO_4$ is applied, the amount of Mg(II) remaining in the hydrolysate (~10 mM) is within the dosage applied in laboratory fermentation and should prove beneficial to fermentation (Rees & Stewart, 1997; Thanonkeo et al., 2007).

TABLE 4

Metal contents in the solid residues at the completion of enzymatic hydrolysis (48 h) of SPORL pretreated substrates

| Samples | Metal salts | Estimated hydrolysis solids yield (%) | Metal content in solid residue (mg/g) | Retained (%) |
|---|---|---|---|---|
| Unwashed | KCl | 63.1 | 1.73 | 1.4 |
|  | $MgSO_4$ | 56.5 | 0.46 | 1.07 |
|  | $CaCl_2$ | 60.5 | 0.90 | 1.36 |
|  | $CaSO_4$ | 59.7 | 1.13 | 1.68 |
| Washed @ 25° C. | KCl | 56.2 | 1.93 | 1.39 |
|  | $MgSO_4$ | 51.3 | 0.55 | 1.18 |
|  | $CaCl_2$ | 52.6 | 0.74 | 0.97 |
|  | $CaSO_4$ | 51.5 | 0.95 | 1.23 |
| Washed @ 98° C. | KCl | 53.9 | 1.80 | 1.25 |
|  | $MgSO_4$ | 51.5 | 0.57 | 1.22 |
|  | $CaCl_2$ | 51.4 | 0.65 | 0.84 |
|  | $CaSO_4$ | 47.5 | 0.85 | 1.01 |

Example 10

Quantification of the Savings of Enzymes and Water with the Application of $MgSO_4$ The reduction of enzymatic hydrolysis inhibition by unbound lignosulfonate with washing and/or application of metal salts can save enzyme to achieve a desired SED. To quantify the amount of enzyme savings while achieving SED of 90% for the SPORL aspen substrate, the amounts of cellulase required for the unwashed and two washed substrates with and without $MgSO_4$ application are determined based on measured SED data (Table 5). The savings in cellulase by either washing or $MgSO_4$ application can be calculated based on MARUL and the applied $MgSO_4$ dosage on cellulose base. For every mg of lignosulfonate removal (based on unit gram of cellulose) through washing at 25° C., it can save 0.088 FPU cellulase. The cellulase savings can also be calculated in terms of water consumption to be 3.0 FPU/L water (2.5 L water was used in producing the washed substrate). On the other hand, the application of one mg $MgSO_4$/g cellulose can save 0.311 FPU cellulase for the unwashed substrate. When washing is substituted by the application of $MgSO_4$, the equivalent substitution ratios are 8.0 and 11.6 mg $MgSO_4$/L water for washing at 25 and 98° C., respectively. The high efficient washing at 98° C. requires more $MgSO_4$ to substitute washing to achieve the same SED. Because $CaSO_4$ is much less expensive and readily available, the efficacy of $CaSO_4$ for substitute washing may be promising.

TABLE 5

Estimated enzyme savings with washing or Mg(II) application at substrate (SPORL pretreated aspen) enzymatic digestibility of 90%

| Samples | Cellulase loading @ SED = 90% (FPU/g cellulose) | Lignin removed (mg/g cellulose)/water used (L) | Savings in cellulase by washing (FPU/g cellulose) | Cellulase savings by washing (FPU/mg lignin removed; FPU/L) | $MgSO_4$ loadings (mg/g cellulose) | Savings in cellulase with $MgSO_4$ (FPU/g cellulose) | Cellulase savings with Mg(II) (FPU/mg $MgSO_4$) |
|---|---|---|---|---|---|---|---|
| Unwashed | 24.0 | | | | | | |
| Washed @25° C. | 16.5 | 85.1/2.5 | 7.5 | 0.088/3.0 | | | |
| Washed @98° C. | 15.0 | 168.1/2.5 | 9.0 | 0.054/3.6 | | | |
| Unwashed + Mg(II) | 17.0 | | | | 22.51 | 7.0 | 0.311 |
| Washed @25° C. + Mg(II) | 13.0 | | | | 16.51 | 3.5 | 0.212 |
| Washed @98° C. + Mg(II) | 12.6 | | | | 16.76 | 2.4 | 0.143 |

Example 11

Using $Ca(OH)_2$ to Enhance Enzymatic Hydrolysis of a SPORL Pretreated Solid Substrate when Combined with its Corresponding Pretreatment Hydrolysate (Hemicellulosic Sugar Stream)

Liming or overliming of pretreatment hydrolysate that contains dissolved lignin produces the similar phenomena of lignin-Ca(II) complexation, which can reduce the affinity of lignin to cellulase enzymes. Although liming or overliming has been widely used as a detoxification method to remove fermentation inhibitors, such as Furfural, HMF, to facilitate fermentation, its application was never intended to form lignin-Ca(II) complex to reduce the affinity of lignin to cellulase enzymes to eliminate nonproductive adsorption of enzyme by dissolved lignin to achieve SSCombF of pretreated substrate and its corresponding pretreatment hydrolysate (hemicelluloses sugar streams). When sulfite was used in pretreatment, such as $SO_2$ catalyzed steam explosion, and SPORL (Zhu et al., 2009), dissolved lignin is in the form of lignosulfonate, which can act as a surfactant to enhance enzymatic hydrolysis (Eriksson et al., 2002; Tu et al., 2009; Zheng et al., 2008). However, lignosulfonate also has the property of lignin that can absorb (non-productive) cellulase enzymes to reduce enzyme activities as we demonstrated in Example 2 (FIGS. 4-6). As a result, the net effect of lignosulfonate can be negative to reduce enzymatic hydrolysis of cellulose. The application of a divalent metal compounds, such as $Ca(OH)_2$ or CaO, forms lignosulfonate-metal complex to reduce or eliminated nonproductive adsorption of cellulase enzymes. As a result, the positive effect of lignosulfonate that acts as a surfactant to enhance enzymatic hydrolysis of cellulose can be demonstrated.

A SPORL pretreated lodgepole substrate produced by reacting beetle killed lodgepole pine wood chips (BD4, Tian et al., 2010) with a solution of sodium bisulfite and sulfuric acid at liquid to wood ratio of 3:1 (V/W). The bisulfite and acid charge on wood chips were 2.21% and 8%, respectively. Pretreatment was conducted at 180° C. for 20 min using a 23 L wood pulping digester as described elsewhere (Zhu et al., 2009). The pretreated wood chips were separated from the pretreatment hydrolysate (water soluble hemicellulsoe sugar stream) using a conventional screen and disk milled. Water was added at milling to achieve discharge solid consistency of 10%. The solid substrate was directly dewatered to a solids content of about 30% by vacuum pressing in a canvas bag. The solid substrate was then washed again thoroughly. Enzymatic hydrolysis of the thoroughly washed substrate was then conducted at 2% solids as control with cellulase loading: Novozyme 1.5 L at 7.5 FPU/g substrate and Novozyme 188 as beta-glucosidase at 10.5 CBU/g substrate. The pretreatment hydrolysate that contains dissolved lignosulfonate was then conditioned by adding $Ca(OH)_2$ to adjust pH to 5.7. A filter with pore size of 0.45 μm was used to filter the $Ca(OH)_2$ conditioned pretreatment hydrolysate. This filtered hydrolysate was then separated using membranes of different molecular weight (MW) cut off: 100k, 30k, 10k, 3k, 1k Da, to produce filtrate containing lignosulfonate with different MW. Approximately 4 mL of conditioned pretreatment hydrolysate along with 31.7 mL acetate buffer solution were used to mix with 0.8 g (oven dry weight) thoroughly washed solid substrate to conduct enzymatic hydrolysis under the same enzyme loadings as the control experiment. The makeup of 4 mL hydrolysate for 0.8 g substrate is based on the yields of solid substrate and pretreatment hydrolysate. The glucose concentrations of the conditioned and filtered pretreatment hydrolysates were measured by a commercial glucose analyzer (YSI-2700, Yellow Springs Instrument Co., Ohio) and listed in Table 6. The amounts of glucose produced by different enzymatic hydrolysis experiments from the washed substrate were obtained by subtracting the amount of glucose in the applied pretreatment hydrolysate from the measured amount of glucose in the mixed hydrolysate. Duplicate experiments were conducted.

TABLE 6

Glucose concentrations in conditioned and filtered pretreatment hydrolysate

| Sample | Test I (g/L) | Test II (g/L) | Mean (g/L) | Standard deviation |
|---|---|---|---|---|
| Unfiltered | 10.9 | 10.3 | 10.6 | 0.42 |
| 0.45 μm | 10.9 | 10.3 | 10.6 | 0.42 |
| 100k Da | 8.4 | 8.6 | 8.5 | 0.10 |
| 30k Da | 5.6 | 5.5 | 5.6 | 0.06 |
| 10k Da | 5.1 | 5.3 | 5.2 | 0.15 |

TABLE 6-continued

Glucose concentrations in conditioned and filtered pretreatment hydrolysate

| Sample | Test I (g/L) | Test II (g/L) | Mean (g/L) | Standard deviation |
|---|---|---|---|---|
| 3k Da | 4.8 | 5.0 | 4.9 | 0.14 |
| 1k Da | 5.1 | 5.0 | 5.0 | 0.06 |

Figure 20:
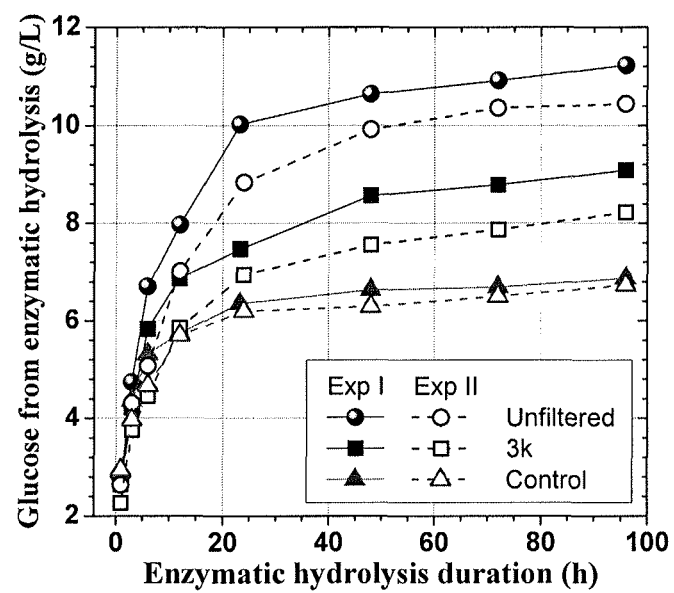
FIG. 20. Experimental repeatability of enzymatic hydrolysis of a washed SPORL pretreated lodgepole pine with the addition of the corresponding pretreatment hydrolysate with and without the addition $Ca(OH)_2$ conditioning.

The repeatability of the enzymatic hydrolysis experiments can be seen from the measured time-dependent glucose concentrations from enzymatic hydrolysis (contributions from glucose in the pretreatment hydrolysate were excluded). The control experiments have excellent repeatability (FIG. 20). The experiments with the addition of the $Ca(OH)_2$ conditioned pretreatment hydrolasate have relatively large systematic errors, i.e., the glucose concentrations from Experiment II were always lower than the corresponding values in Experiment I. Mean values were reported in the discussions below. The substrate enzymatic digestibilities (SEDs) at 72 h from different hydrolysis experiments without (control) and with conditioned pretreatment hydrolysate filtered with different filter size or different MW cut off membranes are shown listed in FIG. 21. The results clearly indicate that the addition of $Ca(OH)_2$ conditioned pretreatment hydrolysate increased the SED. In other words, more glucose was produced from the thoroughly washed substrate by the enzymes with the addition of $Ca(OH)_2$ conditioned sodium lignosulfonate. We hypothesized the formation of lignosulfonate-Ca(II) complex acts as a surfactant to enhance enzymatic hydrolysis. This was demonstrated in Example 9 (FIG. 16) using different metal salts. Here liming was used.

Figure 22:
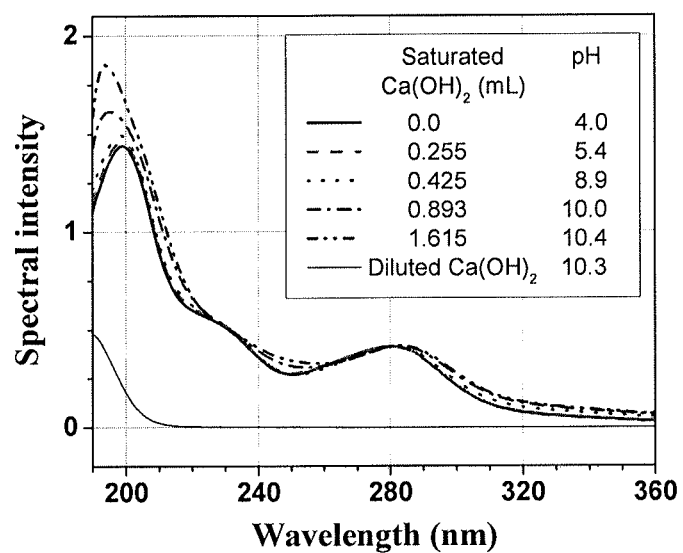
FIG. 22. Effect of the $Ca(OH)_2$ application dosage on the UV-absorption of a SPORL pretreatment hydrolysate.

The formation of lignosulfonate-Ca(II) complex was demonstrated by examining the UV absorption spectra of the $Ca(OH)_2$ conditioned and unconditioned pretreatment hydrolysates (FIG. 22). The spectrum of a $Ca(OH)_2$ solution was also plotted in FIG. 22. As can be seen that the spectra of $Ca(OH)_2$ conditioned pretreatment hydrolysate are different from that of the unconditioned hydrolysate. If there was no formation of lignosulfonate-Ca(II) complex, the spectra of the conditioned hydrolysate would be simply the superposition of the spectrum of the unconditioned hydrolysate and the spectrum of a $Ca(OH)_2$ solution. $Ca(OH)_2$, or more precisely $Ca^{2+}$ and $OH^-$, only absorbs in the far UV range of less than 220 nm as shown in FIG. 22. However, the spectra of the conditioned hydrolysates deviate from the spectrum of the unconditioned spectra in many UV wavelength ranges other than less than 220 nm. Furthermore, absorption increased with the increased application of $Ca(OH)_2$.

Figure 21:
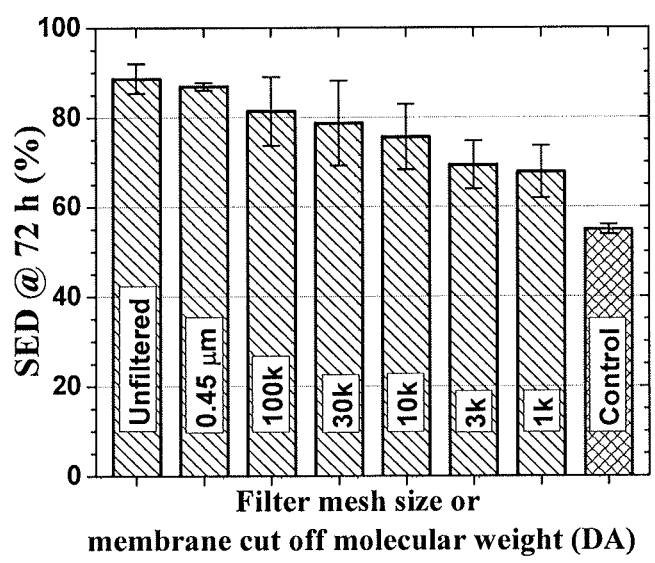
FIG. 21. Effects of the addition of $Ca(OH)_2$ conditioned SPORL pretreatment hydrolysate on the substrate enzymatic digestibility (SED) of a SPORL pertreated lodgepole pine solid substrate.
Figure 23:
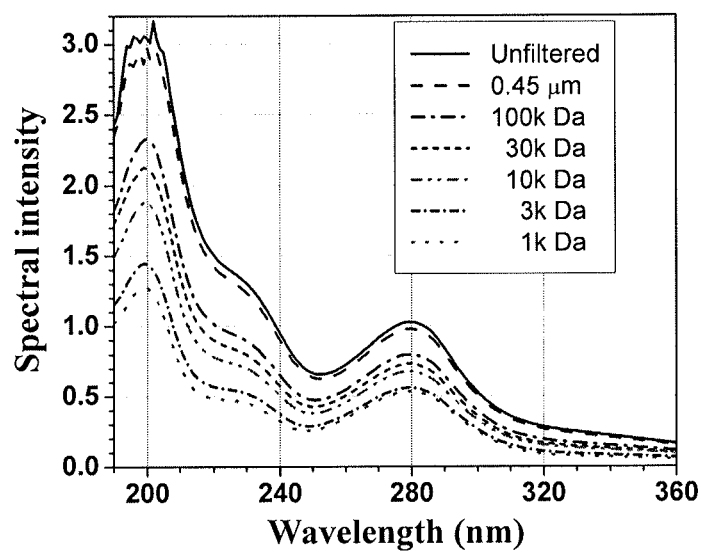
FIG. 23. UV absorption spectra of $Ca(OH)_2$ conditioned SPORL pretreatment hydrolysate after filtered by membranes of various cut off molecular weights.
Figure 24:
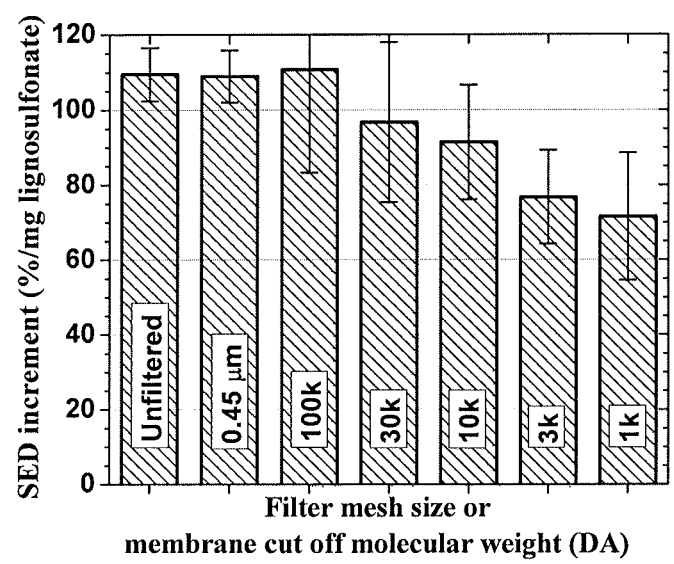
FIG. 24. Effect of $Ca(OH)_2$ conditioned SPORL pretreatment hydrolysate containing lignosulfonate of different molecular weight on the improvement in SED per unit mass of lignosulfonate.
Figure 25:
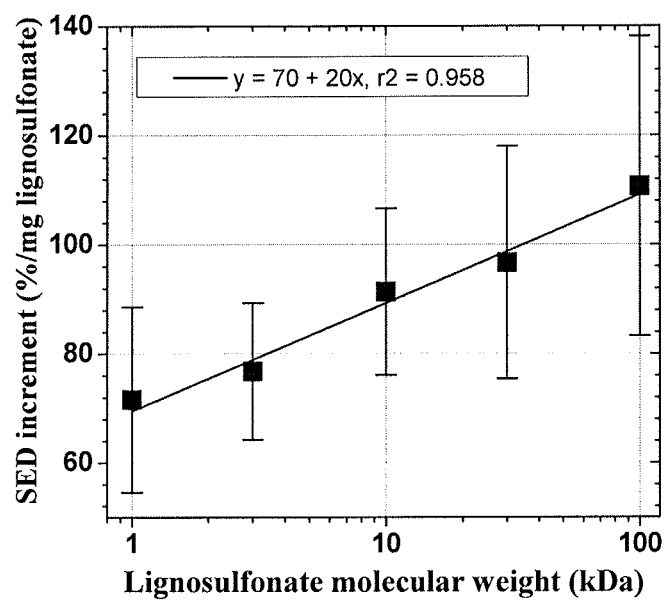
FIG. 25. Correlation of SED improvement per unit mass of lignosulfonate with molecular weight of lignosulfonate in $Ca(OH)_2$ conditioned SPORL pretreatment hydrolysate.

The increment in SED per gram of lignosulfonate-Ca(II) complex of different MWs was calculated based on the results presented in FIG. 21. The amounts of lignosulfonate applied were determined through UV absorption measurements at wavelength 280 nm (FIG. 23) through calibration using a commercial lignosulfonate. This is to compare the effectiveness of lignosulfonate-Ca(II) with different MWs for enhancing enzymatic hydrolysis. The results show that lignosulfonate-Ca(II) of large MW (above 100 K Da) is more effective than those of lower MW (FIG. 24). The differences are not evident when MW is above 100 kDa however. The increment in SED by unit mass of lignosulfonate, $\Delta$SED, with MW<100 kDa has a logarithmic relation with MW (FIG. 25), i.e., $\Delta$SED$-70=20 \cdot \log$(MW), $r^2=0.958$. This can be explained by the fact that lignosulfonate with larger MW is more effective as a dispersant. Enhanced surface activity to block lignin in solid lignocelluloses to reduce nonproductive cellulase adsorption is the mechanism for enhanced enzymatic hydrolysis using surfactants (Eriksson et al., 2002). It should be reminded that the large standard deviations shown in FIG. 24 were due to systematic measurement errors (FIG. 20).

Example 12

Using $Ca(OH)_2$ to Achieve SSCombF of a SPORL Pretreated Solid Substrate and its Corresponding Pretreatment Hydrolysate (Hemicellulosic Sugar Stream)

A similar lodgepole pine solid and liquid substrate were produced under same conditions described in Example 11 except for using a digester of capacity of 1 L. Again, additional washing of the solid substrate was not applied. Table 7 listed the chemical composition of the solid and liquid substrates. The pretreatment hydrolysate was conditioned using $Ca(OH)_2$ powder under two conditions: (1) simple neutralization to pH 5; (2) overliming to pH 10. The overlimed hydrolysate was centrifuged at 10,000 g for 5 min to separate the precipitated $CaSO_4$. The supernatant of the overlimed hydrolysate was then mixed with sulfuric acid to adjust it to pH 5. Table 8 listed the sugar and inhibitor profiles of the conditioned hydrolysate. The application of $Ca(OH)_2$ produced lignosuonate-Ca(II) complex that has very low or no affinity to cellulase enzymes but can act as surfactant to enhance enzymatic hydrolysis. Therefore, mixing the $Ca(OH)_2$ conditioned sample with solid substrate to conduct simultaneous enzymatic saccharification and combined fermentation (SSFCombF) should produce excellent ethanol yield.

Liquefaction of the solid substrate was first conducted. Two identical enzymatic hydrolysis were conducted at a solid substrate loading of 10% (w/w) in 45 mL of sodium acetate buffer (pH 4.8, concentration 50 mM) using 5 g (od) solid substrate in 250-mL Erlenmeyer flasks. The substrate suspensions were incubated on a shaker (Thermo Fisher Scientific, Model 4450, Waltham, Mass.) set at 50° C. and 200 rpm. A mixture of Celluclast 1.5 L with an activity loading of approximately 15 FPU/g substrate and Novozyme 188 with an activity loading of approximately 22.5 IU/g substrate was used. After 6 h of enzymatic hydrolysis, 35 mL of one of the two conditioned pretreatment hydrolysates, either neutralized or overlimed, was added to each of the two enzymatically liquefied cellulosic substrate directly (without separating the enzymatic residue solids and lignin). The combined hydrolysates (i.e., 50 mL enzymatic+35 mL pretreatment hydrolysate) were then inoculated by adding a yeast *S. cerevisiae*. No nutrients were added. The starting yeast cell mass concentration was 2.0 g dry-cell wt/L. In an ideal industrial process, the solid and liquor streams will be combined and fermented together. To simulate this, it would be necessary for the 35 mL pretreatment liquor to be mixed with an enzymatic hydrolysate produced at 14% solids consistency based on solid substrate yield of 59.6% and L/W of 3. However, the enzymatic hydrolysate used in this study was produced at 10% solids consistency due to the difficulties in conducting 14% hydrolysis on shaking bed without a mechanical mixer. Therefore, the makeup of the combined hydrolysate (50 mL enzymatic+35 mL pretreatment hydrolysate) represents overdosing of fermentation inhibitors and lignosulfonate. All fermentation experiments were carried out at 30° C. for 96 h. Samples were taken periodically and centrifuged at 10,000 rpm for 5 min and were stored at −4° C. until analyzed for sugar and ethanol.

TABLE 7

Chemical composition of untreated wood chips and yields of key wood components in the solid substrate and pretreatment liquid hydrolysate

|  | Untreated wood chips [a] | SPORL pretreated solid substrate | SPORL pretreatment hydrolysate |
|---|---|---|---|
| Glucan | 41.9 ± 0.6 | 36.7 ± 0.26/87.6% [b] | 2.7 ± 0.1/6.4% [b] |
| Xylan | 5.5 ± 0.5 | 0.3 ± 0.03/5.5% [b] | 2.2 ± 0.6/40% [b] |
| Mannan | 11.7 ± 0.3 | 0.3 ± 0.01/2.6% [b] | 6.0 ± 0.3/51.3% [b] |
| K. Lignin | 28.6 ± 0.2 | 21.3 ± 0.46/74.5% [b] | 7.3/(by balance) |
| Arabinan | 1.7 ± 0.2 | Nd | 0.6 ± 0.2/35.3% [b] |
| Galactan | 2.9 ± 0.4 | Nd | 1.4 ± 0.4/48.3% [b] |
| Furfural |  |  | 0.9/16.4% [d] |
| HMF |  |  | 1.1/9.4% [d] |
| Yield | 100 | 58.6/60.6 [c] | 22.2 |

[a] The scale of the ruler is centimeter
[b] The first number is sugar as polysaccharide; the second number after the back slash is saccharide yield, i.e., percentage of original sugar in wood.
[c] The first number is the sum; the second number is the measured solid substrate yield
All data are in wt % of untreated wood unless otherwise indicated
[d] The first number is furan as pentosan or hexsan; the second number after the back slash is furan as percentage of xylan and mannan in untreated wood.

TABLE 8

Effects of conditioning on pretreatment hydrolysate sugar and inhibitor profiles

| Sample | Glucose | Xylose | Mannose | Furfural | HMF | Acetic acid |
|---|---|---|---|---|---|---|
| Initial liquor | 10.1 ± 0.40 | 8.3 ± 0.20 | 22.3 ± 0.70 | 2.24 ± 0.14 | 2.71 ± 0.15 | 5.26 ± 0.39 |
| Neutralized | 7.9 ± 0.79 | 6.3 ± 0.55 | 17.5 ± 2.02 | 2.17 ± 0.26 | 2.50 ± 0.02 | 5.09 ± 0.03 |
| Overlimed | 5.4 ± 0.36 | 3.9 ± 0.28 | 11.7 ± 0.89 | 1.36 ± 0.11 | 1.62 ± 0.02 | 4.18 ± 0.01 |

All data are in g/L

Figure 26:
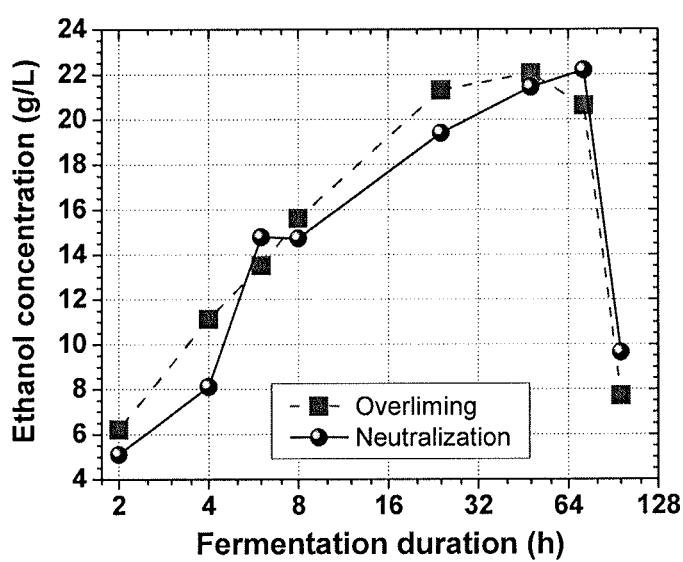
FIG. 26. Comparisons of time-dependent ethanol concentrations in fermentation broths.

The time-dependent ethanol concentrations in the fermentation broth were examined to demonstrate the potential for combined fermentation of enzymatic and pretreatment hydrolysate without detoxification. It was found that the ethanol concentration profile for the run using neutralized (without detoxification) pretreatment hydrolysate is not much different from those obtained using overlimed (FIG. 26). Detoxifications by overliming only improved ethanol productivity in the early stage from 2.0 to about 2.8 g/L/h (4 h, Table 9) but had negligible effects on the overall ethanol productivity (24 h, Table 9).

TABLE 9

Average ethanol productivity, rates of sugar consumption and furan metabolization in 4 (the first number) and 24 h (the number after back slash) of fermentation

| Fermentation run | Neutralized | Overlimed | XAD-4 absorbed | Neutralized + Fed-batch |
|---|---|---|---|---|
| Ethanol productivity | 2.03/0.81 | 2.78/0.89 | 2.75/0.84 | 3.95/0.82 |
| Glucose consumption | −7.02/−1.39 | −7.64/−1.35 | −7.75/−1.35 | −12.98/ |
| Mannose consumption | −0.28/ | −0.73/ | −0.92/ |  |
| Furfural metabolization | −0.222/ | −0.135/ | −0.10/ |  |
| HMF metabolization | −0.162/ | −0.135/ | −0.08/ |  |

All data are in g/L/h

The SPORL pretreatment process data along with the results from the fermentation using the Ca(OH)$_2$ neutralized pretreatment hydrolysate were used to determine process mass balance and net ethanol energy output (FIG. 27). The ethanol yield was 213 kg/ton wood or 270.4 L/ton wood, which is equivalent to 70.1% theoretical yield based on the wood glucan and mannan contents of 41.9% and 11.7% (Table 7), respectively. This ethanol yield is equivalent to that reported previously from live lodgepole pine trees utilizing completely separate fermentation of pretreatment hydrolysate after detoxification using XAD-4 resin (Zhu et al., 2010b), suggesting the presence of dissolved lignosulfonate after the addition of Ca(OH)$_2$ to form Lignosulfonate-Ca(II) complex did not negatively affect enzymatic saccharification and therefore ethanol yield.

Example 13

Using CaSO$_4$ to Enhance Enzymatic Hydrolysis of an Unwashed SPORL Lodgepole Pine at High Solids Loadings Another similar lodgepole pine substrate was produced under the exact conditions described in Example 12 except no water was added in disk milling of the pretreated wood chips. Therefore, the resultant solid substrate was not washed and contains dissolved lignin (lignosulfonate). High solids enzymatic hydrolysis was conducted at 10% of the solid substrate at 50° C. on a shaking bed (described in Example 1) with buffer solution at pH 4.8. CaSO$_4$ was first added at various loadings from 5-150 mM. After mixing for 30 min, cellulase enzymes were applied. Enzyme loadings were Novozyme Celluclast 1.5 L at 9 FPU/g substrate with Novozyme 188 as β-glucosidase at 9 CBU/g glucan. It was found the application of CaSO$_4$ increased glucose production from the substrate after 72 h enzymatic hydrolysis (FIG. 22). Furthermore, glucose concentration in the hydrolysate was increased almost linearly with CaSO$_4$ application dosage up to 30 mM and then increased slowly to reach an asymptotic value. We also applied CaSO$_4$ to a pure cellulosic substrate of Whatman paper to conduct enzymatic hydrolysis at 10% solids consistency to verify artifact in glucose measurements by CaSO$_4$. It was found that glucose concentration was not affected by the application of CaSO$_4$ in a dosage range from 10-100 mM as listed in Table 10.

TABLE 10

Glucose concentrations in the enzymatic hydrolysates of a pure cellulosic substrate hydrolyzed at 10% solids applied with different dosage of $CaSO_4$

| Hydrolysis duration (h) | $CaSO_4$ application dosage (mM) | | | | |
|---|---|---|---|---|---|
| | 0 | 10 | 30 | 60 | 100 |
| 24 | 64.5 | 90 | 85 | 87 | 90 |
| 48 | 102 | 103.5 | 115 | 102 | 95 |
| 72 | 108.5 | 108 | 107 | 106 | 100 |

The time dependent glucose concentrations and repeatability test results are listed in Table 11. The data consistently indicate that the application of $CaSO_4$ can improve glucose production from an unwashed SPORL substrate at a solids loading of 10%.

TABLE 11

The time dependent glucose concentrations in the enzymatic hydrolysate of an unwashed SPORL pretreated lodgpole pine hydrolysated at at 10% solids loading

| $CaSO_4$ (mM) | Glucose concentration in enzymatic hydrolysate (g/L) | | | |
|---|---|---|---|---|
| | 24 h | 36 h | 48 h | 72 h |
| 0 | | | 9.8 | 10.3 |
| 0 | | | 9.5 | 10.2 |
| 5 | | | 10.2 | 10.5 |
| 10 | | 11.8 | 11.8 | 12.0 |
| 15 | 12.9 | 13.6 | 13.8 | 14.0 |
| 20 | 13.0 | 14.5 | 15.0 | 15.2 |
| 30 | 15.5 | 15.8 | 16.2 | 17.2 |
| 30 | 15.2 | | 16.2 | 16.6 |
| 60 | 15.4 | | 16.5 | 16.8 |
| 100 | 20.2 | | 21.9 | 22.5 |
| 150 | 21.6 | | 22.3 | 23.4 |

These examples demonstrated lignin-metal complexation for eliminating inhibition of cellulase by unbound lignosulfonate in unwashed pretreated lignocellulosic substrates. With the application of 1 mmol/g substrate metal salts, e.g., $MgSO_4$, the reduction in substrate enzymatic digestibility (SED) by unbound lignosulfonate in an unwashed SPORL aspen substrate was recovered. The enhancement of SED by lignin-metal complexation can substitute washing to save water or reduce enzyme loading in biomass conversion to biofuels.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Adler, Wood Sci. Technol., 11(3):169-218, 1977.
Berlin et al., Applied Biochem. Biotechnol., 121:163-170, 2005.
Bhardwaj et al., Colloids and Surface A: Physicochem. Eng. Aspects, 236:39-44, 2004.
Borjesson et al., Enzyme and Microbial Technol., 40(4):754-762, 2007.
Crist et al., J. Chem. Technol. Biotechnol., 78:199-202, 2003.
Crotogino et al., TAPPI J., 70(6):95-103, 1987.
Davis, J. Wood Chem. Tech., 18(2):235-352, 1998.
Enzyme Nomenclature 1992, Academic Press, San Diego, Calif. with Supplement 1 (1993), Supplement 2 (1994), Supplement 3 (1995, Supplement 4 (1997) and Supplement 5 [in Tipton, Eur. J. Biochem. (1994) 223:1-5, Barrett, Eur. J. Biochem. (1995) 232:1-6, Barrett, Eur. J. Biochem. (1996) 237:1-5, Barrett, Eur. J. Biochem. (1997) 250:1-6, and Eur. J. Biochem. (1999) 264:610-650, respectively
Eriksson et al., Enzyme and Micro. Technol., 31:(3):353-364, 2002.
Ghose, Pure Applied Chem., 59:257-268, 1987.
Grierson et at, Cement Concrete Res., 35:631-636, 2005.
Guo et al., J. Hazardous Mat., 151:134-142, 2008.
Helle et al., Biotechnol. Bioengineer., 42:611-617, 1993.
Holtzapple et al., Biotechnol. Bioengineer., 36:275-287, 1990.
Katz et al., Svensk Papperstidn., 87:R48-53, 1984.
Lin and Van Ness, In: Chemical Engineer's Handbook, Perry and Chilton (Eds), 5th Ed., Chap. 4, McGraw-Hill, N.Y., 1973.
Liu et al., J. Agric. Food Chem., 58:7233-7238, 2010.
Lozovik and Kaflyuk, J Analytical Chem., 60(9):938-943, 2005.
Lynd et al., Biocommodity Engin., Biotechnol. Prog., 15: 777-793, 1999.
Lynd et al., Microbiol. Mol. Biol. Rev., 66:506-577, 2002.
Mansfield et al., Biotechnology Prog., 15:804-816, 1999.
Miller, Anal. Chem., 31:426-428, 1959.
Mizutani et al., Cellulose, 9:83-89, 2002.
Nagle et al., Biotechnolo. Prog., 18:734-738, 2002.
Ooshima et al., Biotechnol. Bioengineer., 36:446-452, 1990.
Pan et al., Applied Biochem. Biotechnol., 113(16):1103-1114, 2004.
Pan et al., Applied Biochem. Biotechnol., 121:1069-1079, 2005.
Pan et al., Biotechnol. Bioengineer., 94(5):851-861, 2006.
Philippidis, In: Handbook on Bioethanol: Production and Utilization, Wyman (Ed.), Taylor & Francis, Washington, D.C., 179-212, 1996.
Rees and Stewart, J. Inst. Brew., 103:287-291, 1997.
Reinikainen et al., Proteins-Struct. Func. Gene., 22(4):392-403, 1995.
Ryu and Mandels, Enz. Microb. Technol., 2:91-102, 1980.
Salmon, Biotechnol. Tech., 5(5):383-388, 1991.
Sewalt et al., J. Agricul. Food Chem., 45(5):1823-1828, 1997.
Sheehan and Himmel, Bioethanol. Biotechnol. Prog., 15: 817-827, 1999.
Simola et al., Polymer, 41:2121-2126, 2000.
Sinitsyn et al., Applied Bioche. Biotechnol., 7:455-458, 1982.
Tengborg et al., Enzyme Microb. Tech., 28(9-10):835-844, 2001.
Thanonkeo et al., Biotechnol., 6(1):112-119, 2007.
Tian et al., Bioresource Technol., 101:8678-8685, 2010. Torre et al., J. Agric. Food Chem., 40:1762-1766, 1992.
Tu et al., Biotechnol. Progress, 25:1122-1129, 2009.
U.S. Pat. No. 4,461,648
U.S. Pat. No. 5,916,780

U.S. Publn. 2009/0298149

Varma et al., *J. Environ. Sci. Health, A*23:43-265, 1989.

Wang et al., *Biotech. Prog.,* 25(4):1086-1093, 2009.

Wood and Bhat, In: *Methods in Enzymology, Vol.* 160, *Biomass (Part a, Cellulose and Hemicellulose)*, Colowick and Kaplan (Eds.), Academic Press, Inc., NY, 160:87-112, 1988.

Xu et al., *Colloids and Surfaces A: Physicochem. Eng. Aspects,* 301:255-263, 2007.

Yang and Wyman, *Biotech. Bioengineer.,* 94:(4), 611-617, 2006.

Zakis, In: *Functional analysis of lignins and their derivatives*, TAPPI Press, Atlanta, Ga., 77-79, 1994

Zheng et al., *Applied Biochem. Biotechnol.,* 146:231-248, 2008.

Zhu et al., *Applied Microbiol. Biotechnol.,* 86(5):1355-1365, 2010.

Zhu et al., *Bioresource Technol.,* 100(8):2411-2418, 2009.

Zhu et al., *Bioresource Technol.,* 101(8):2782-2792, 2010.

Zhu et al., *Bioresource Technol.,* 101:4992-5002, 2010.

What is claimed is:

1. A lignocellulose-containing composition comprising:
   a) an unwashed and pretreated biomass containing free lignin and at least 10% solid lignocellulose;
   b) an aqueous solution comprising a divalent cation that increases enzymatic cellulose hydrolysis as compared to enzymatic cellulose hydrolysis in the absence of such a divalent cation, wherein said divalent cation is calcium or magnesium and is present at 1 to 10 mol per kilogram solid lignocellulose; and
   c) a cellulase.

2. The composition of claim 1, wherein the calcium or magnesium is in the form of $CaCl_2$, $CaCO_3$, $CaSO_4$, $MgSO_4$, $Ca(OH)_2$, CaO, or a combination thereof.

3. The composition of claim 1, wherein the aqueous solution has a pH of 2 to 8.

4. The composition of claim 3, wherein the aqueous solution has a pH of 4 to 7.

5. The composition of claim 1, further comprising a fermentative organism.

6. The composition of claim 1, wherein the solid lignocellulose comprises lignosulfonate.

7. A method for cellulose hydrolysis, wherein the method comprises the steps of:
   a) pretreating an unwashed biomass containing free lignin and at least 10% solid lignocellulose to form an unwashed and pretreated biomass containing free lignin and at least 10% solid lignocellulose;
   b) mixing the unwashed and pretreated biomass containing free lignin and at least 10% solid lignocellulose, an aqueous solution comprising a divalent cation present at 1 to 10 mol per kilogram solid lignocellulose, and a cellulase to form a mixture, wherein said divalent cation is calcium or magnesium; and
   c) treating the mixture under conditions which hydrolyze cellulose.

8. The method of claim 7, wherein the biomass is pretreated with sulfite or bisulfite.

9. The method of claim 8, wherein the biomass comprises grasses, agriculture residues, municipal solid waste, waste paper, softwood, and/or hardwood.

10. The method of claim 7, further comprising reducing the size of the biomass.

11. The method of claim 7, further comprising separating the unwashed and pretreated biomass into a solid portion and a liquid portion.

12. The method of claim 7, further comprising fermenting the treated mixture.

13. The method of claim 12, wherein fermenting the treated mixture produces biofuel.

14. The method of claim 12, wherein the method comprises hydrolyzing cellulose and fermenting in the same reactor.

15. The method of claim 12, wherein the method comprises hydrolyzing cellulose and fermenting in separate reactors.

16. The method of claim 7, wherein the mixture further comprises hemicellulose and the treating step hydrolyzes the hemicellulose.

\* \* \* \* \*

UNITED STATES PATENT AND TRADEMARK OFFICE
CERTIFICATE OF CORRECTION

PATENT NO. : 8,815,561 B2  
APPLICATION NO. : 13/215729  
DATED : August 26, 2014  
INVENTOR(S) : Hao Liu and Junyong Zhu Page 1 of 1

It is certified that error appears in the above-identified patent and that said Letters Patent is hereby corrected as shown below:

In title page, item (75) Inventors, delete "Junyoug" and insert --Junyong-- therefor.

Signed and Sealed this  
Thirtieth Day of December, 2014

Michelle K. Lee  
*Deputy Director of the United States Patent and Trademark Office*